US008431373B2

(12) United States Patent
Yi et al.

(10) Patent No.: US 8,431,373 B2
(45) Date of Patent: Apr. 30, 2013

(54) RECOMBINANT MICROORGANISMS FOR INCREASED PRODUCTION OF ORGANIC ACIDS

(75) Inventors: Jian Yi, Charlotte, MI (US); Susanne Kleff, Okemos, MI (US); Michael V. Guettler, Holt, MI (US)

(73) Assignee: Michigan Biotechnology Institute, Lansing, MI (US)

( * ) Notice: Subject to any disclaimer, the term of this patent is extended or adjusted under 35 U.S.C. 154(b) by 0 days.

(21) Appl. No.: 13/328,894

(22) Filed: Dec. 16, 2011

(65) Prior Publication Data

US 2012/0164703 A1 Jun. 28, 2012

Related U.S. Application Data

(63) Continuation of application No. 11/722,579, filed as application No. PCT/US2005/045714 on Dec. 16, 2005, now Pat. No. 8,119, 377.

(60) Provisional application No. 60/647,141, filed on Jan. 26, 2005, provisional application No. 60/639,443, filed on Dec. 22, 2004.

(51) Int. Cl.
*C12N 1/20* (2006.01)
*C12N 15/74* (2006.01)

(52) U.S. Cl.
USPC .......................... 435/145; 435/476; 435/252

(58) Field of Classification Search ..................... None
See application file for complete search history.

(56) References Cited

U.S. PATENT DOCUMENTS 7,163,812 B2 * 1/2007 Zeikus et al. ................. 435/145

FOREIGN PATENT DOCUMENTS

| JP | 2005217918 | 8/2005 |
| JP | 2003521888 | 7/2007 |
| WO | 03025006 A2 | 5/2003 |
| WO | 2004003175 A2 | 1/2004 |
| WO | 2005042736 A1 | 5/2005 |

OTHER PUBLICATIONS

*Actinobacillus succinogenes* sp. nov., a novel succinic-acid-producing strain from the bovine rumen (International Journal of Systematic Bacteriology 1999 vol. 49: 207-216).*

Kim, et al, "Construction of a Shuttle Vector for the Overexpression of Recombinant Proteins in *Actinobacillus succinogenes*", Plasmid, 2004, vol. 51, 2004, pp. 108-115.

Lu Yiqin, "Biochemical Identification of Glucose 6-phosphate Hydrogenase (G-6-PD) with *E.coli* Expression System", Chemistry of Life Years, 1995, vol. 15(1), pp. 42-44.

Mayes, Peter A., "The Pentose Phosphate Pathway & Other Pathways of Hexose Metabolism", Harper's Biochemistry, 1990, 22 ed., 189-198.

Park, et al, "Utilization of Electrically Reduced Neutral Red by *Actinobacillus succinogenes*: Physiological Function of Neutral Red in Membrane-Driven Fumarate Reduction and Energy Conservation", Journal of Bacteriology, Apr. 1999, vol. 181, No. 3, pp. 2403-2410.

Rowley, et al, "Molecular Characterization of the *Escherichia coli* K-12 zwf Gene Encoding clucose 6-Phosphate Dehydrogenase", Journal of Bacteriology, Feb. 1991, vol. 173, No. 3, pp. 968-977.

Zeikus, et al, "Biotechnology of Succinic Acid Production and Markets for Derived Industrial Products", Applied Microbiology Biotechnology, Apr. 1999, vol. 51, pp. 545-552.

Guettler et al (*Actinobacillus succinogenes* sp. nov., a novel succinic-acid-producing strain from the bovine rumen (International Journal of Systematic Bacteriology 1999 vol. 49: 207-216.

Stols et al. Production of Succinic Acid through Overexpression of Nad+-Dependent Maleic Enzyme in an *Escherishia coli* Mutant. Applied Environmental Microbiology, Jul. 1997, vol. 6, No. 7, pp. 2695-2701.

Van Der Werf et al. Environmental and Factors affecting the succinate product ratio during carbohydrate ferentation by *Actinobacillus* sp. 130Z. Arch Microbiol. 1997, vol. 167, pp. 332-342.

* cited by examiner

*Primary Examiner* — Kagnew H Gebreyesus

(74) *Attorney, Agent, or Firm* — Dickinson Wright PLLC

(57) ABSTRACT

Disclosed are recombinant microorganisms for producing organic acids. The recombinant microorganisms express a polypeptide that has the enzymatic activity of an enzyme that is utilized in the pentose phosphate cycle. The recombinant microorganism may include recombinant *Actinobacillus succinogenes* that has been transformed to express a Zwischenferment (Zwf) gene. The recombinant microorganisms may be useful in fermentation processes for producing organic acids such as succinic acid and lactic acid. Also disclosed are novel plasmids that are useful for transforming microorganisms to produce recombinant microorganisms that express enzymes such as Zwf.

16 Claims, 3 Drawing Sheets

Figure 1. Metabolic flux analysis of *A. succinogenes* variant FZ45 batch fermentation using glucose.
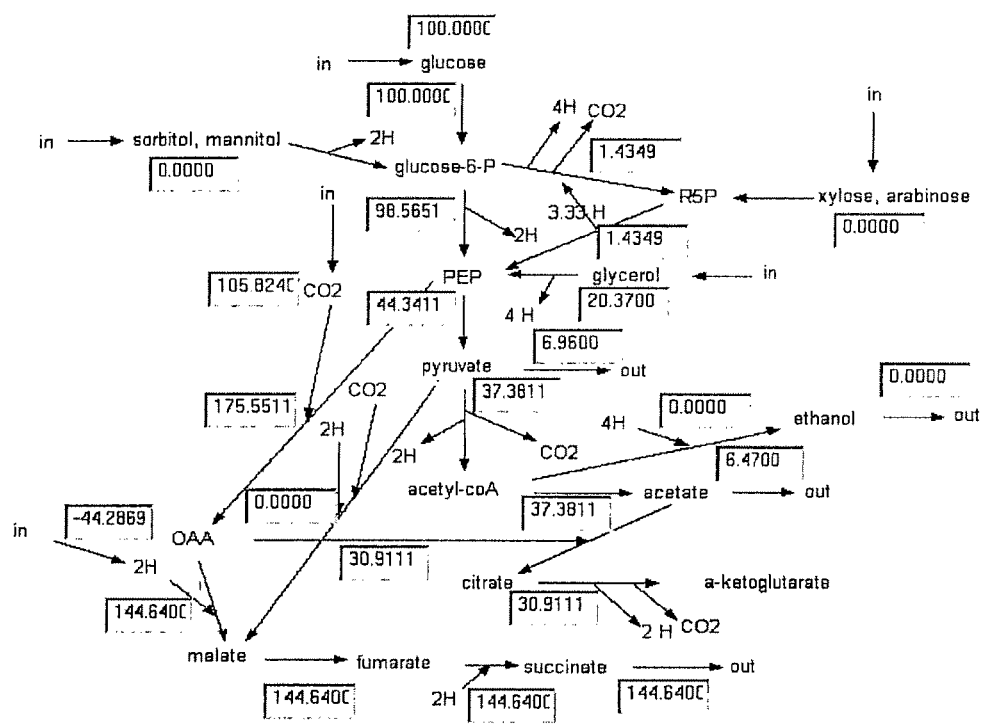

Figure 2. Metabolic flux analysis of recombinant *A. succinogenes* FZ45/pJR762.73 batch fermentation using glucose.
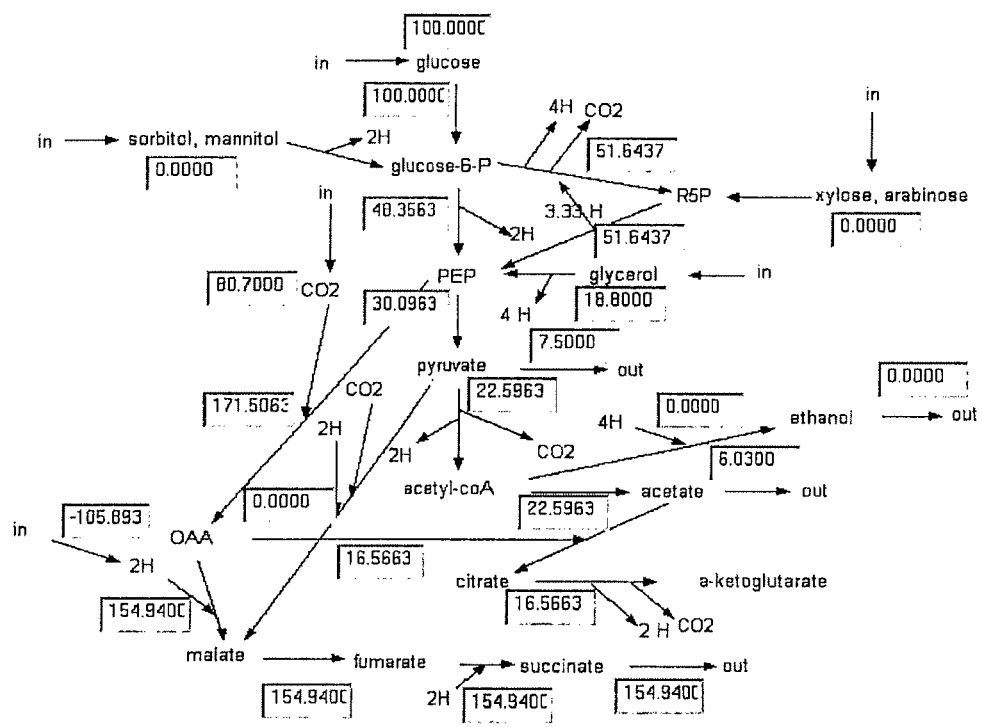

Figure 3. Zwf enzymatic activities in cell extracts of transformed strains.
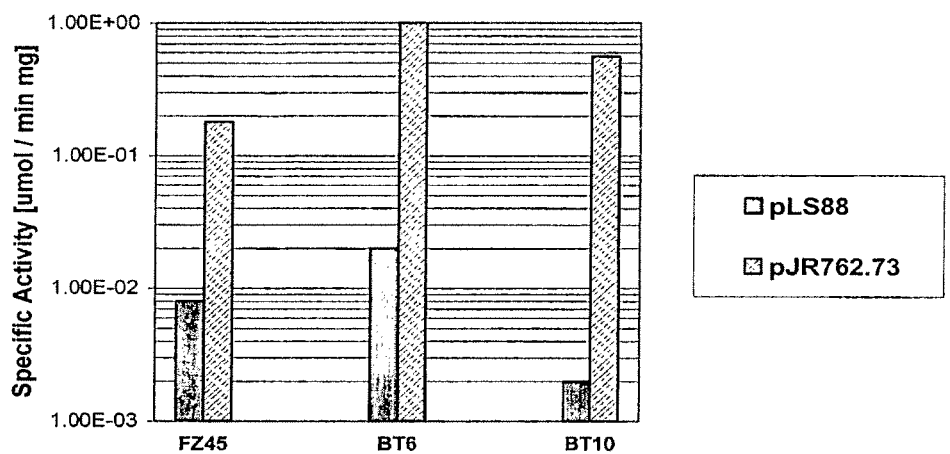

SEQUENCE LISTING

```
<160> NUMBER OF SEQ ID NOS: 10

<210> SEQ ID NO 1
<211> LENGTH: 1476
<212> TYPE: DNA
<213> ORGANISM: Escherichia coli

<400> SEQUENCE: 1
atggcggtaa cgcaaacagc ccaggcctgt gacctggtca ttttcggcgc gaaaggcgac        60
cttgcgcgtc gtaaattgct gccttccctg tatcaactgg aaaaagccgg tcagctcaac       120
ccggacaccc ggattatcgg cgtagggcgt gctgactggg ataaagcggc atataccaaa       180
gttgtccgcg aggcgctcga aactttcatg aaagaaacca ttgatgaagg tttatgggac       240
accctgagtg cacgtctgga tttttgtaat ctcgatgtca atgacactgc tgcattcagc       300
cgtctcggcg cgatgctgga tcaaaaaaat cgtatcacca ttaactactt tgccatgccg       360
```

```
cccagcactt ttggcgcaat tgcaaaggg cttggcgagg caaaactgaa tgctaaaccg      420
gcacgcgtag tcatggagaa accgctgggg acgtcgctgg cgacctcgca ggaaatcaat      480
gatcaggttg gcgaatactt cgaggagtgc caggtttacc gtatcgacca ctatcttggt      540
aaagaaacgg tgctgaacct gttggcgctg cgttttgcta actccctgtt tgtgaataac      600
tgggacaatc gcaccattga tcatgttgag attaccgtgg cagaagaagt ggggatcgaa      660
gggcgctggg gctattttga taaagccggt cagatgcgcg acatgatcca gaaccacctg      720
ctgcaaattc tttgcatgat tgcgatgtct ccgccgtctg acctgagcgc agacagcatc      780
cgcgatgaaa aagtgaaagt actgaagtct ctgcgccgca tcgaccgctc caacgtacgc      840
gaaaaaaccg tacgcgggca atatactgcg ggcttcgccc agggcaaaaa agtgccggga      900
tatctggaag aagagggcgc gaacaagagc agcaatacag aaactttcgt ggcgatccgc      960
gtcgacattg ataactggcg ctgggccggt gtgccattct acctgcgtac tggtaaacgt     1020
ctgccgacca aatgttctga agtcgtggtc tatttcaaaa cacctgaact gaatctgttt     1080
aaagaatcgt ggcaggatct gccgcagaat aaactgacta tccgtctgca acctgatgaa     1140
ggcgtggata tccaggtact gaataaagtt cctggccttg accacaaaca taacctgcaa     1200
atcaccaagc tggatctgag ctattcagaa acctttaatc agacgcatct ggcggatgcc     1260
tatgaacgtt tgctgctgga aaccatgcgt ggtattcagg cactgttttgt acgtcgcgac     1320 gaagtggaag aagcctggaa atgggtagac tccattactg aggcgtgggc gatggacaat     1380
gatgcgccga accgtatca ggccggaacc tggggacccg ttgcctcggt ggcgatgatt     1440
acccgtgatg gtcgttcctg gaatgagttt gagtaa                              1476

<210> SEQ ID NO 2
<211> LENGTH: 1473
<212> TYPE: DNA
<213> ORGANISM: Escherichia coli

<400> SEQUENCE: 2
atggcggtaa cgcaaacagc ccaggcctgt gacctggtca ttttcggcgc gaaaggcgac       60
cttgcgcgtc gtaaattgct gccttccctg tatcaactgg aaaaagccgg tcagctcaac      120
ccggacaccc ggattatcgg cgtagggcgt gctgactggg ataaagcggc ataccaaaa      180 gttgtccgcg aggcgctcga aactttcatg aaagaaacca ttgatgaagg tttatgggac      240
accctgagtg cacgtctgga ttttttgtaat ctcgatgtca atgacactgc tgcattcagc      300
cgtctcggcg cgatgctgga tcaaaaaaat cgtatcacca ttaactactt tgccatgccg      360
cccagcactt ttggcgcaat tgcaaaggg cttggcgagg caaaactgaa tgctaaaccg      420
gcacgcgtag tcatggagaa accgctgggg acgtcgctgg cgacctcgca ggaaatcaat      480
gatcaggttg gcgaatactt cgaggagtgc caggtttacc gtatcgacca ctatcttggt      540
aaagaaacgg tgctgaacct gttggcgctg cgttttgcta actccctgtt tgtgaataac      600
tgggacaatc gcaccattga tcatgttgag attaccgtgg cagaagaagt ggggatcgaa      660
gggcgctggg gctattttga taaagccggt cagatgcgcg acatgatcca gaaccacctg      720
ctgcaaattc tttgcatgat tgcgatgtct ccgccgtctg acctgagcgc agacagcatc      780
cgcgatgaaa aagtgaaagt acctgaagtc tcgtcgccgc atcgaccgct caacgtacg      840 cgaaaaaacc gtacgcgggc aatatactgc gttccccagg gcaaaaagt gccgggatat      900 ctggaagaag agggcgcgaa caagagcagc aatacagaaa ctttcgtggc gatccgcgtc      960
gacattgata actggcgctg gccggtgtg ccattctacc tgcgtactgg taaacgtctg     1020
```

```
ccgaccaaat gttctgaagt cgtggtctat ttcaaaacac ctgaactgaa tctgtttaaa   1080
gaatcgtggc aggatctgcc gcagaataaa ctgactatcc gtctgcaacc tgatgaaggc   1140
gtggatatcc aggtactgaa taaagttcct ggccttgacc acaaacataa cctgcaaatc   1200
accaagctgg atctgagcta ttcagaaacc tttaatcaga cgcatctggc ggatgcctat   1260
gaacgtttgc tgctggaaac catgcgtggt attcaggcac tgtttgtacg tcgcgacgaa   1320
gtggaagaag cctggaaatg ggtagactcc attactgagg cgtgggcgat ggacaatgat   1380
gcgccgaaac cgtatcaggc cggaacctgg ggacccgttg cctcggtggc gatgattacc   1440
cgtgatggtc gttcctggaa tgagtttgag taa                                1473
```

```
<210> SEQ ID NO 3
<211> LENGTH: 491
<212> TYPE: PRT
<213> ORGANISM: Escherichia coli

<400> SEQUENCE: 3

Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
    130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
            180                 185                 190

Ala Asn Ser Leu Phe Val Asn Asn Trp Asp Asn Arg Thr Ile Asp His
        195                 200                 205

Val Glu Ile Thr Val Ala Glu Glu Val Gly Ile Glu Gly Arg Trp Gly
    210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
            260                 265                 270

Arg Ile Asp Arg Ser Asn Val Arg Glu Lys Thr Val Arg Gly Gln Tyr
        275                 280                 285

Thr Ala Gly Phe Ala Gln Gly Lys Lys Val Pro Gly Tyr Leu Glu Glu
    290                 295                 300
```

```
Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
            325                 330                 335

Thr Gly Lys Arg Leu Pro Thr Lys Cys Ser Glu Val Val Val Tyr Phe
                340                 345                 350

Lys Thr Pro Glu Leu Asn Leu Phe Lys Glu Ser Trp Gln Asp Leu Pro
            355                 360                 365

Gln Asn Lys Leu Thr Ile Arg Leu Gln Pro Asp Glu Gly Val Asp Ile
        370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Glu Ala Trp Lys Trp
        435                 440                 445

Val Asp Ser Ile Thr Glu Ala Trp Ala Met Asp Asn Asp Ala Pro Lys
450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490

<210> SEQ ID NO 4
<211> LENGTH: 258
<212> TYPE: DNA
<213> ORGANISM: Actinobacillus succinogenes

<400> SEQUENCE: 4
ttaatttctt taatcgggac gctatcgata aattgaaaat gcagcaatag aggaaacacg      60
gtttgtttga gtgaaaacag ccgtgttttt tcatttaccg ccataaaaat ttgaaacgga     120
tcacaaatca tgaaaaaaat acgttcaaat tagaactaat tatcgaaaat ttgatctagt     180
taacattttt taggtataaa tagttttaaa atagatctag tttggatttt taattttaaa     240
ttatcaatga ggtgaagt                                                   258

<210> SEQ ID NO 5
<211> LENGTH: 1488
<212> TYPE: DNA
<213> ORGANISM: Actinobacillus succinogenes

<400> SEQUENCE: 5
ttacgctttt ttcttcatgg agcccgaagg tctgcgccat acgcgtcctt cacgggcgat      60
aagtttatcc gcttccaccg gtccccaggt gccggcttca tattcgtaaa cgcgaccttg     120
gttttccttg taatccaaaa tcggctgcac gaatttccag caggcgtgaa cggcgtcggt     180
acgggcgaat aatgtggcgt cgcctttcat ggcgtcaagc agtaaacgtt cgtaggcggt     240
taataaatta gcggaagaac tgatatccgc ataacggaaa tccatggata cttctttagc     300
ctcgaagccg gctcccggtt ttttcaaacc gaagaacatg gaaatgcctt cgtccggttg     360
gatacggatg attaatttgt tatccggcgc attttggctg aataccgggt gcggcgtggt     420
tttgaaatga atgacgattt ccgtcacccg ggtcggcagg cgtttaccgg tgcgcacgta     480
aaacggcacg ccggcccagc gccagttatc gatttggcag cgcaacgcca tgtaggtttc     540
```

```
ggtgccggaa tcggacggca cgcccgcttc ctccagataa cccttcaccg gtttatcgtc    600
aacggtggag gccgtgtatt gccctaatac cagattgtgt ttgagatctt ccgtggtcaa    660
cggatgcaga caatagagca ctttggcggt ttcgtcacgc atggaatcgg cgttaataat    720
cgccggcggt tccatggcaa ccattgccaa tacttgcaat aagtggtttt ggaacatatc    780
ccgcattgca ccggaaccgt cataatagcc gccccgttgt tctacgccga tctcttccgc    840
gccggtgatt tctacgtaat cgatgaagtt acggttccaa agcggttcga acaggccgtt    900
ggagaatcgc agcaccaaca gattttgcac ggtttctttg cccaaataat ggtcgatacg    960
gtaaatctgg tgttcctcga agaaacggtg aatctgaata ccagtgcttt ggcggttttt   1020
aatatcgtaa ccgaacggtt tttccacgat aatccgtttc agccgaatt cttccgtatt   1080 taagccgtga gccgccaggc attccggaat aacgccgtac aggctcggcg gagtggatag   1140
ataataaagc gtattgccgc aggtttggta tttgtcgtgt aattcatcca aacgaggcag   1200
taactttacg taatccgccg aatcggaggt gtttaccgcc tggtaataca gatgagaaca   1260
gaatttatcc agcgtttcgc cttcggcatt ttcttgggta atcagggcgg ttcgcatttt   1320
ttcacggaaa atgtcatccg tcatttctgt gcgggccact cccagcacgg agaagttttc   1380
ttccaaccgt ccgatttgt aaagattata gagtgcggga attaatttac ggtgcgtcag   1440 atccctgat gcgccgaaaa tcacgataca attatttct gctttcat                  1488
```

<210> SEQ ID NO 6
<211> LENGTH: 495
<212> TYPE: PRT
<213> ORGANISM: Actinobacillus succinogenes

<400> SEQUENCE: 6

Met Lys Ala Glu Asn Asn Cys Ile Val Ile Phe Gly Ala Ser Gly Asp
1               5                   10                  15

Leu Thr His Arg Lys Leu Ile Pro Ala Leu Tyr Asn Leu Tyr Lys Ile
            20                  25                  30

Gly Arg Leu Glu Glu Asn Phe Ser Val Leu Gly Val Ala Arg Thr Glu
        35                  40                  45

Met Thr Asp Asp Ile Phe Arg Glu Lys Met Arg Thr Ala Leu Ile Thr
    50                  55                  60

Gln Glu Asn Ala Glu Gly Glu Thr Leu Asp Lys Phe Cys Ser His Leu
65                  70                  75                  80

Tyr Tyr Gln Ala Val Asn Thr Ser Asp Ser Ala Asp Tyr Val Lys Leu
                85                  90                  95

Leu Pro Arg Leu Asp Glu Leu His Asp Lys Tyr Gln Thr Cys Gly Asn
            100                 105                 110

Thr Leu Tyr Tyr Leu Ser Thr Pro Pro Ser Leu Tyr Gly Val Ile Pro
        115                 120                 125

Glu Cys Leu Ala Ala His Gly Leu Asn Thr Glu Phe Gly Trp Lys
    130                 135                 140

Arg Ile Ile Val Glu Lys Pro Phe Gly Tyr Asp Ile Lys Thr Ala Lys
145                 150                 155                 160

Ala Leu Asp Ile Gln Ile His Arg Phe Phe Glu Glu His Gln Ile Tyr
                165                 170                 175

Arg Ile Asp His Tyr Leu Gly Lys Glu Thr Val Gln Asn Leu Leu Val
            180                 185                 190

Leu Arg Phe Ser Asn Gly Leu Phe Glu Pro Leu Trp Asn Arg Asn Phe
        195                 200                 205

Ile Asp Tyr Val Glu Ile Thr Gly Ala Glu Glu Ile Gly Val Glu Gln
210                 215                 220

Arg Gly Gly Tyr Tyr Asp Gly Ser Gly Ala Met Arg Asp Met Phe Gln
225                 230                 235                 240

Asn His Leu Leu Gln Val Leu Ala Met Val Ala Met Glu Pro Pro Ala
                245                 250                 255

Ile Ile Asn Ala Asp Ser Met Arg Asp Glu Thr Ala Lys Val Leu Tyr
                260                 265                 270

Cys Leu His Pro Leu Thr Thr Glu Asp Leu Lys His Asn Leu Val Leu
            275                 280                 285

Gly Gln Tyr Thr Ala Ser Thr Val Asp Asp Lys Pro Val Lys Gly Tyr
290                 295                 300

Leu Glu Glu Ala Gly Val Pro Ser Asp Ser Gly Thr Glu Thr Tyr Met
305                 310                 315                 320

Ala Leu Arg Cys Gln Ile Asp Asn Trp Arg Trp Ala Gly Val Pro Phe
                325                 330                 335

Tyr Val Arg Thr Gly Lys Arg Leu Pro Thr Arg Val Thr Glu Ile Val
                340                 345                 350

Ile His Phe Lys Thr Thr Pro His Pro Val Phe Ser Gln Asn Ala Pro
            355                 360                 365

Asp Asn Lys Leu Ile Ile Arg Ile Gln Pro Asp Glu Gly Ile Ser Met
370                 375                 380

Phe Phe Gly Leu Lys Lys Pro Gly Ala Gly Phe Glu Ala Lys Glu Val
385                 390                 395                 400

Ser Met Asp Phe Arg Tyr Ala Asp Ile Ser Ser Ala Asn Leu Leu
                405                 410                 415

Thr Ala Tyr Glu Arg Leu Leu Leu Asp Ala Met Lys Gly Asp Ala Thr
                420                 425                 430

Leu Phe Ala Arg Thr Asp Ala Val His Ala Cys Trp Lys Phe Val Gln
            435                 440                 445

Pro Ile Leu Asp Tyr Lys Glu Asn Gln Gly Arg Val Tyr Glu Tyr Glu
450                 455                 460

Ala Gly Thr Trp Gly Pro Val Glu Ala Asp Lys Leu Ile Ala Arg Glu
465                 470                 475                 480

Gly Arg Val Trp Arg Arg Pro Ser Gly Ser Met Lys Lys Ala
                485                 490                 495

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaagaattct aatttctttt aatcgggac                                       29

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcgtcgacat acttcacctc attgat                                          26

```
<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgctcgagg gcggtaacgc aaacagc                                             27

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgctcgagt tactcaaact cattccagg                                           29
```

RECOMBINANT MICROORGANISMS FOR INCREASED PRODUCTION OF ORGANIC ACIDS

STATEMENT REGARDING U.S. GOVERNMENT SUPPORT

This invention was made with support from the United States Government under Cooperative Agreement No. DE-FC36-02GO12001 awarded by the Department of Energy. The United States Government has certain rights in this invention.

This application is a continuation of U.S. non-provisional application Ser. No. 11/722,579, filed on Aug. 28, 2008, now U.S. Pat. No. 8,119,377, which is a U.S. national stage application of PCT International Application No. PCT/US2005/045714, filed Dec. 16, 2005, which claims priority from U.S. provisional application Ser. No. 60/647,141, filed on Jan. 26, 2005; and U.S. provisional application No. 60/639,443, filed on Dec. 22, 2004. The aforementioned applications are incorporated herein by reference in their entireties.

This application contains a Sequence Listing submitted in ASCII format via EFS-Web, created on Mar. 9, 2012, named 35548-67.txt, 16,429 bytes in size, and which is incorporated by reference in its entirety.

BACKGROUND

Many chemicals that are currently derived from petrochemical materials could be produced from naturally occurring carbohydrates. In particular, succinic acid, a four-carbon dicarboxylic acid, has the potential to become a high volume commodity chemical that could be used as starting material for commercial processes that produce many important intermediate and specialty chemicals for the consumer product industries and that currently rely on starting materials derived from non-renewable petrochemical materials. For example, as a commodity chemical, succinic acid could replace petrochemical starting materials used in the production of 1,4-butanediol (BDO) and tetrahydrofuran (THF) compounds, which are useful as solvents and starting materials for many industries. For example, BDO and THF compounds are useful for producing resins for automotive bodies, thermoplastics for use in household appliances, and elastic polymers such as Lycra™ in the textile industry. In addition, BDO and THF compounds also have many specialty uses in the agrochemical and pharmaceutical industries. Notably, worldwide consumption of BDO is expected to increase at an annual rate as high as 4%.

The petrochemicals currently used to produce BDO and THF include acetylene, formaldehyde, butane, butadiene, and propylene oxide. All of these have various hazardous properties, such as extreme flammability, chemical instability and toxicity. Further, as these materials are derived from petroleum, they deplete a non-renewable resource, and upon disposal or destruction, ultimately release carbon (as carbon dioxide) into the atmosphere. Thus, developing succinic acid as a replacement for petrochemically derived materials would reduce handling and storage of hazardous materials, enhance industrial and community safety, reduce pollution and environmental costs, and reduce dependence on oil.

Production of succinic acid and other organic compounds by fermentation of sugars is economically feasible. A number of microorganisms have been used to produce succinic acid using corn sugars as a carbon source. As such, developing succinic acid as replacement for petrochemical starting materials would expand markets for corn, and other agricultural products and/or biomass that can provide fermentable sugars.

Formally, the biochemical pathway for succinic acid production adds a carbon dioxide molecule to the three carbon compound phosphoenolpyruvate (PEP), to produce the four carbon compound oxaloacetate (OAA). The next steps in the pathway to succinic acid are part of the reverse tricarboxylic acid cycle (TCA cycle) and include two obligate reduction steps. In the biochemical process leading from OAA to succinate, OAA must first be reduced to produce L-malate. L-malate is then dehydrated to produce fumarate and water. Fumarate is then reduced to give the succinic acid. In the chemical arts, "reduction" refers to the addition of molecular hydrogen to a compound.

Generally, free molecular hydrogen is not found in intracellular biological systems. Rather, reduction is performed through the use of coenzymes that function as biochemical equivalents of hydrogen (i.e., as carriers of molecular hydrogen) and are termed "reducing equivalents." Reducing equivalents include the coenzymes nicotinamide adenine dinucleotide hydrogen ("NADH"), nicotinamide adenine dinucleotide phosphate hydrogen ("NADPH"), flavine adenine dinucleotide hydrogen ("FADH$_2$"), and flavin mononucleotide hydrogen ("FMNH"). Generally, NADH and NADPH may be interconverted in a range of microorganisms by the enzyme pyridine dinucleotide transhydrogenase.

the reducing equivalents required to transform OAA to succinate are provided by NAD(P)H$_2$, FADH$_2$, or other cofactors. It is essential that a sufficient quantity of reducing equivalents is available for the transformation of OAA to succinate. If sufficient reducing equivalents are not available, the biochemical pathway will not function efficiently, and only a portion of the OAA will be transformed into the desired succinate.

Reducing equivalents may be produced in a number of biological processes that are commonly found in cellular metabolism. For example, reducing equivalents may be generated in the pentose phosphate cycle (PPC). In the PPC, glucose-6-phosphate is converted to D-6-phospho-glucono-δ-lactone by the enzyme glucose-6-phosphate dehydrogenase, which is also known as Zwischenferment enzyme or Zwf. As part of this conversion, NADP is converted to NADPH as an acceptor of reducing equivalents.

Few microorganisms have been described which produce sufficient concentrations of succinic acid for commercial production. One such microorganism is *Actinobacillus succinogenes*, a facultative anaerobe that was isolated from the bovine rumen. This organism produces high concentration of succinic acid and tolerates high sugar concentration. *Actinobacillus succinogenes* is one of the best known producers of succinic acid, but the fermentative yields of this strain may be limited by the lack of reducing equivalents. As such, improvements are desirable to increase the yield of succinic acid produced by fermentation, including the use of improved strains of microorganisms for producing succinic acid.

SUMMARY

Disclosed are recombinant microorganisms for producing organic acids. The recombinant microorganisms expresses a polypeptide that has one or more biochemical activities of an enzyme utilized in the pentose phosphate cycle. In one embodiment, the enzyme is glucose-6-phosphate-1-dehydrogenase, also called Zwischenferment enzyme or Zwf. For example, the recombinant microorganism may express a polynucleotide that encodes a polypeptide having Zwf enzyme activity. In one embodiment, the recombinant microorganism is a recombinant strain of a succinic acid producing microorganism which has been transformed with a DNA molecule that expresses a polypeptide having Zwf enzyme activity.

The recombinant microorganism typically is capable of producing one or more organic acids at a level suitable for commercial production. In some embodiments, the recombinant microorganism is a succinic acid producing microorganism. For example, the microorganism may produce succinic acid at a concentration suitable for commercial production. A concentration suitable for commercial production may be at least about 20 g/L, 40 g/L, 60 g/L, 80 g/L, 100 g/L, 120 g/L, and/or 140 g/L. Desirably, the recombinant microorganism is capable of producing succinic acid at concentrations of about 50 g/L to about 130 g/L.

The recombinant microorganism may be selected and/or recombinantly engineered to tolerate relatively high concentrations of succinic acid to facilitate production of succinic acid at a concentration suitable for commercial production in a fermentation system. In some embodiments, the recombinant microorganism may be selected to produce relatively low amounts of undesirable by-products such as acetate, formate, and/or pyruvate (e.g., no more than about 2.0 g/L acetate, no more than about 2.0 g/L formate, and/or no more than about 3.0 g/L pyruvate). The recombinant microorganism may be derived from a strain (or a variant of a strain) that is resistant to levels of sodium monofluoroacetate at concentration of at least about 1 g/L, 2 g/L, 4 g/L, and/or 8 g/L. In another embodiment, a variant of the recombinant microorganism may be selected to be resistant to levels of sodium monofluoroacetate at concentration of at least about 1 g/L, 2 g/L, 4 g/L, and/or 8 g/L.

In one embodiment, the recombinant microorganism is derived from a strain of *Actinobacillus succinogenes* (i.e., "*A. succinogenes*") or a microorganism related to *Actinobacillus succinogenes*. One suitable strain of *A. succinogenes* is Bacterium 130Z deposited with the American Type Culture Collection (ATCC), under ATCC Accession Number 55618. See U.S. Pat. No. 5,504,004 for description of Bacterium 130Z and other suitable strains.

Other suitable microorganisms may be selected for preparing the recombinant microorganism and may include microorganisms which are related to *A. succinogenes* as determined by sequence identity within 16S rRNA. For example, a suitable microorganism related to *A. succinogenes* may have 16S rRNA that exhibits substantial sequence identity to *A. succinogenes* 16S rRNA (i.e., a microorganism having 16S rRNA that exhibits at least about 90% sequence identity to *A. succinogenes* 16S rRNA or more suitably, that exhibits at least about 95% sequence identity to *A. succinogenes* 16S rRNA). Many representative microorganisms of the family *Pasteurellaceae* have 16S rRNA that exhibits at least about 90% sequence identity to *A. succinogenes* 16S rRNA. For example, See Guettler et al., INT'L J. SYSTEMATIC BACT. (1999), 49, 207-216 at page 209, Table 2. Suitable microorganisms may include microorganisms such as Bisgaard Taxon 6 and Bisgaard Taxon 10.

In some embodiments, the recombinant microorganism may be prepared from organisms other than *A. succinogenes*. For example, the recombinant microorganism may be prepared from any microorganism that is suitable for use in fermentation systems for producing organic acids. A suitable microorganism may include *E. coli*. Suitable strains of *E. coli* are known in the art.

Variants of microorganisms that are resistant to sodium monofluoroacetate may also be suitable for preparing the recombinant microorganism. For example, See U.S. Pat. Nos. 5,521,075 and 5,573,931. In one embodiment, the recombinant microorganism is prepared from a variant of *A. succinogenes* that is resistant to at least about 1 g/L sodium monofluoroacetate. One suitable variant is FZ45. See U.S. Pat. No. 5,573,931. The recombinant microorganism deposited under ATCC Accession Number PTA-6255, is derived from a variant of *A. succinogenes* that is resistant to at least about 1 g/L sodium monofluoroacetate (i.e., FZ45).

The recombinant microorganism typically is transformed with a polynucleotide encoding a polypeptide that has one or more biochemical activities of an enzyme utilized in the pentose phosphate cycle. For example, the recombinant microorganism may be transformed with a polynucleotide that encodes a polypeptide having one or more biochemical activities of the Zwf enzyme (i.e., glucose-6-phosphate dehydrogenase activity and/or NADP reductase activity). Desirably, the polynucleotide encodes a polypeptide that facilitates the conversion of NADP to NADPH. The polynucleotide or polypeptide may be endogenous to the microorganism or derived from a gene or enzyme normally present in the microorganism. In some embodiments, the polynucleotide or polypeptide may be homologous to an endogenous gene or enzyme of the microorganism. In other embodiments, the polynucleotide or polypeptide may be heterologous (i.e., derived from a gene or enzyme normally not present in the microorganism or derived from a source other than the microorganism).

The recombinant microorganism may express a variant of the polynucleotide that encodes the polypeptide and/or a variant of the polypeptide. A variant of the polynucleotide may include a polynucleotide having at least about 90% sequence identity to the polynucleotide, or desirably, at least about 95% sequence identity to the polynucleotide, where the polynucleotide encodes a polypeptide that has one or more biochemical activities of the Zwf enzyme (e.g., NADP reductase activity). A variant may include a polypeptide that has at least about 90% sequence identity to the polypeptide, or desirably, at least about 95% sequence identity to the polypeptide, where the polypeptide has one or more biochemical activities of the Zwf enzyme (e.g., NADP reductase activity). As such, suitable polynucleotides may include polynucleotides encoding a polypeptide having at least about 95% sequence identity to a selected Zwf enzyme, where the polypeptide has NADP reductase activity.

The recombinant microorganism may be transformed with a polynucleotide that expresses a polypeptide having Zwf enzyme activity, where the recombinant microorganism exhibits higher Zwf enzyme activity than a microorganism which has not been transformed with a polynucleotide that expresses a polypeptide having Zwf enzyme activity. In some embodiments, the recombinant microorganism exhibits at least about five times (5×) more Zwf enzyme activity, (or desirably at least about ten times (10×) more Zwf enzyme activity, or more desirably at least about fifty times (50×) more Zwf enzyme activity), than a microorganism which has not been transformed with a polynucleotide that expresses a polypeptide having Zwf enzyme activity. Zwf enzyme activity may include NADP reductase activity. Zwf enzyme activity may be determined by measuring the level of NADPH present the recombinant microorganism (e.g., as compared to a microorganism which has not been transformed with a polynucleotide that expresses a polypeptide having Zwf enzyme activity).

The recombinant microorganism may express a polynucleotide that encodes a Zwf enzyme such as a Zwf gene. A variant of the polynucleotide may comprise a polynucleotide having at least about 90% sequence identity to a Zwf gene, or desirably, at least about 95% sequence identity to a Zwf gene and encoding a polypeptide that has one or more biochemical activities of the Zwf enzyme. A variant of a polynucleotide may include a nucleic acid fragment of the polynucleotide. For example, a fragment may include at least about 90% of a Zwf gene, or at least about 95% of a Zwf gene. A nucleic acid fragment may be any suitable length. For example, the nucleic acid fragment may comprise at least about 10, 50, 100, 250, 500, 1000 and/or 1400 nucleotides. A fragment may encode a polypeptide that has one or more biochemical activities of the Zwf enzyme.

Suitable Zwf genes may include Zwf genes endogenous or native to the recombinant microorganism (i.e., Zwf genes normally present in the microorganism from which the recombinant microorganism is derived), or variants thereof. Other suitable Zwf genes may include Zwf genes heterologous to the microorganism (i.e., Zwf genes normally not present in, or obtained from sources other than the microorganism used to prepare the recombinant microorganism), or variants thereof. Suitable Zwf genes may include variants that have at least about 90% sequence identity to the polynucleotide sequence of the selected Zwf gene (preferably at least about 95% sequence identity to the polynucleotide sequence of the selected Zwf gene) and that encode a polypeptide that has one or more biochemical activities of the Zwf enzyme (i.e., glucose-6-phosphate dehydrogenase activity and/or NADP reductase activity).

Suitable Zwf genes may include the *E. coli* Zwf gene or variants thereof. The polynucleotide sequence of the *E. coli* Zwf gene is deposited with GenBank under accession number NC_000913, reverse complement of nucleotides 1,932,863 to 1,934,338 (SEQ ID NO:1) and under accession number M55005, nucleotides 708 to 2180 (SEQ ID NO:2). Suitable variants of the *E. coli* Zwf gene may include a polynucleotide having at least about 90% sequence identity (desirably at least about 95% sequence identity) to the polynucleotide of SEQ ID NO:1 (or SEQ ID NO:2), such that the polynucleotide encodes a polypeptide that has one or more biochemical activities of the Zwf enzyme (i.e., glucose-6-phosphate dehydrogenase activity and/or NADP reductase activity).

Suitable Zwf genes may include the *A. succinogenes* Zwf gene or variants thereof. The draft genome sequence for *A. succinogenes* 130Z has recently been established and assembled and is publicly available as of September 2005, at the Joint Genome Institute, Department of Energy website. The Zwf gene is annotated as "glucose-6-phosphate 1-dehydrogenase" and is present on contig 115, nucleotides 8738-10225 (i.e., SEQ ID NO:5). The predicted amino acid sequence of encoded polypeptide (i.e., the *A. succinogenes* Zwf enzyme) is presented as SEQ ID NO:6. The Zwf enzyme exhibits 43% amino acid sequence identity and 60% amino acide homology to the *E. coli* Zwf enzyme using the "BLAST" alignment algorithm version BLASTP 2.2.12, BLOSUM62 matrix, available at the National Center for Biotechnology Information website. Suitable variants of the *A. succinogenes* Zwf gene may include a polynucleotide having at least about 90% sequence identity (desirably at least about 95% sequence identity) to the polynucleotide of SEQ ID NO:5, such that the polynucleotide encodes a polypeptide that has one or more biochemical activities of the Zwf enzyme (i.e., glucose-6-phosphate dehydrogenase activity and/or NADP reductase activity).

The recombinant microorganism may express an endogenous Zwf enzyme (i.e., a Zwf enzyme present within the microorganism from which the recombinant microorganism is derived), or variants thereof. In other embodiments, the recombinant microorganism may express a Zwf enzyme that is heterologous to the microorganism (i.e., a Zwf enzyme that is not present or expressed in the microorganism from which the recombinant microorganism is derived), or variants thereof. Suitable Zwf enzymes may include variants having at least about 90% amino acid sequence identity to the amino acid sequence of a selected Zwf enzyme (desirably at least about 95% amino acid sequence identity to the selected Zwf enzyme) and having one or more biochemical activities of the Zwf enzyme (e.g., NADP reductase activity and/or glucose-6-phosphate dehydrogenase activity). Suitable Zwf enzymes may include the *E. coli* Zwf enzyme (e.g., SEQ ID NO:3, polypeptide encoded by the reverse complement of the nucleotide sequence of nucleotides 1,932,863 to 1,934,338 of NC_000913) or variants thereof, and the *A. succinogenes* Zwf enzyme (e.g., SEQ ID NO:6) or variants thereof.

A variant polypeptide may include a fragment of a Zwf enzyme. For example, a fragment may include at least about 90% of the amino acid sequence of SEQ ID NO:3, or more desirably at least about 95% of the amino acid sequence of SEQ ID NO:3. In other embodiments, a fragment may include at least about 90% of the amino acid sequence of SEQ ID NO:6, or more desirably at least about 95% of the amino acid sequence of SEQ ID NO:6. A polypeptide fragment may be any suitable length. For example, the polypeptide fragment may comprise at least about 10, 50, 100, 200, and/or 300 amino acids (e.g., of SEQ ID NO:3 or SEQ ID NO:6). A polypeptide fragment typically has one or more biochemical activities of the Zwf enzyme.

The recombinant microorganism may include a succinic acid producing microorganism that has been transformed with a polynucleotide that expresses an endogenous (i.e., native) Zwf gene which encodes an endogenous (i.e., native) Zwf enzyme. In some embodiments, the recombinant microorganism may include a succinic acid producing microorganism that has been transformed with a polynucleotide that expresses a heterologous Zwf gene which encodes a heterologous Zwf enzyme. The recombinant microorganism deposited with the American Type Culture Collection (ATCC), under ATCC Accession Number PTA-6255, is a recombinant strain of a succinic acid producing microorganism (i.e., *A. succinogenes*) that expresses a heterologous Zwf gene (e.g., the *E. coli* Zwf gene) which encodes a heterologous Zwf enzyme.

The recombinant microorganism may express a polypeptide having Zwf enzyme activity at relatively high levels (i.e., the polypeptide may be "overexpressed"). For example, the recombinant microorganism may express an endogenous Zwf enzyme at relatively high levels as compared to a non-recombinant microorganism. In some embodiments, the recombinant microorganism may be transformed with a DNA molecule (e.g., a plasmid) that expresses an endogenous Zwf enzyme at relatively high levels compared to a recombinant microorganism that has not been transformed with the DNA molecule.

A polynucleotide, such as a Zwf gene, may be optimized for expression in a selected microorganism from which the recombinant microorganism is derived. For example, a heterologous Zwf gene may be optimized for expression in a non-native microorganism. In some embodiments, a Zwf gene may be optimized for expression in *A. succinogenes*, or in a microorganism such as Bisgaard Taxon 6 or Bisgaard Taxon 10. In other embodiments, a Zwf gene may be optimized for expression in *E. coli*.

A polynucleotide such as a Zwf gene may be optimized for expression in the recombinant microorganism by any suitable strategy. For example, a Zwf gene may be optimized for expression in the recombinant microorganism by operably linking the Zwf gene to a promoter sequence that facilitates expression of the Zwf gene in the recombinant microorganism. The promoter sequence may be optimized to facilitate relatively high levels of expression in the recombinant microorganism (i.e., optimized to facilitate "overexpression"). The Zwf gene may be operably linked to a promoter sequence that is endogenous to the microorganism (i.e., a promoter native to the microorganism) or heterologous to the microorganism (i.e., a promoter normally not present in, or derived from a source other than the microorganism). Suitable promoters may include promoters that are not the native promoter for the selected Zwf gene (i.e., a non-Zwf gene promoter, which may be endogenous to the microorganism or heterologous to the microorganism). Suitable promoters may include inducible promoters or constitutive promoters. Suitable promoters may be derived from promoters of succinic acid producing microorganisms.

In other embodiments, expression of a Zwf gene may be optimized at the translational level. For example, a heterologous Zwf gene may be modified to include codons that demonstrate preferred usage frequency in the microorganism from which the recombinant microorganism is derived as a non-natural host for the gene.

In another embodiment, expression of a polynucleotide such as a Zwf gene may be optimized by providing a relatively high copy number of the polynucleotide in the recombinant microorganism. For example, a Zwf gene may be present on an epigenetic element that is capable of replicating to achieve a relatively high copy number in the recombinant microorganism (e.g., a plasmid).

In some embodiments, the recombinant microorganism is a recombinant strain of a succinic acid producing microorganism, such as *Actinobacillus succinogenes* or related microorganisms, which has been transformed with a DNA molecule that includes a promoter operationally linked to a Zwf gene. The Zwf gene may be derived from an endogenous or heterologous Zwf gene and may include, for example, the *A. succinogenes* Zwf gene (e.g., SEQ ID NO:5) and the *E. coli* Zwf gene (e.g., SEQ ID NOs: 1 & 2). Other Zwf genes are known and their polynucleotide sequences have been published (See, e.g., GenBank). Suitable endogenous or native promoter sequences of succinic acid producing microorganisms may include, for example, the phosphoenolpyruvate (PEP) carboxykinase promoter sequence. The *A. succinogenes* phosphoenolpyruvate (PEP) carboxykinase promoter sequence is deposited with GenBank under accession number AY308832, nucleotides 1-258 (SEQ ID NO:4). A phosphoenolpyruvate (PEP) carboxykinase promoter may be a suitable heterologous promoter for a Zwf gene (i.e., a non-Zwf gene promoter).

As described herein, a recombinant microorganism may include a recombinant DNA molecule as an epigenetic element and/or the recombinant DNA molecule may be incorporated into the genome of the microorganism (e.g., by appropriate methods of recombination). In certain embodiments, the DNA molecule is a plasmid, a recombinant bacteriophage, a bacterial artificial chromosome (3AC) and/or an *E. coli* P1 artificial chromosome (PAC). The DNA molecule may include a selectable marker. Suitable selectable markers may include markers for kanamycin resistance, ampicillin resistance, tetracycline resistance, chloramphenicol resistance, and combinations of these selectable markers. In one embodiment, the selectable marker is kanamycin resistance.

As described herein, a recombinant DNA molecule may include a suitable promoter operationally linked to a polynucleotide that encodes a polypeptide having one or more biochemical activities of Zwf enzyme for expressing the polynucleotide in a recombinant microorganism (e.g., *A. succinogenes*). The promoter may be suitable for expressing the polypeptide in a succinic acid producing microorganism. In some embodiments, the recombinant DNA molecule includes a phosphoenol pyruvate (PEP) carboxykinase promoter (e.g., a *A. succinogenes* phosphoenol pyruvate (PEP) carboxykinase promoter) operationally linked to a Zwf gene or a variant thereof, (which may include a heterologous Zwf gene such as an *E. coli* Zwf gene or an *A. succinogenes* Zwf gene). For example, the DNA molecule may include nucleotides 1-258 of the DNA sequence deposited under GenBank accession number AY308832 (SEQ ID NO:4) or a variant thereof, operationally linked to the reverse complement of nucleotides 1,932,863 to 1,934,338 of the DNA sequence deposited under GenBank accession number NC_000913 (SEQ ID NO:1); or operationally linked to the DNA sequence deposited under GenBank accession number M55005 (SEQ ID NO:2); or operationally linked to the DNA sequence of SEQ ID NO:5. In some embodiments, the promoter may include a polynucleotide having at least about 95% sequence identity to the polynucleotide of SEQ ID NO:4 and having promoter activity in the recombinant microorganism.

A recombinant microorganism comprising the recombinant DNA molecule may be suitable for producing an organic acid (e.g., succinic acid or lactic acid) in a fermentation system. The recombinant microorganism comprising the recombinant DNA molecule may produce enhanced levels of an organic acid (e.g., succinic acid or lactic acid) in a fermentation system relative to a microorganism that does not comprise the recombinant DNA molecule.

Also disclosed is a DNA plasmid comprising one or more of the aforementioned recombinant DNA molecules. The DNA plasmid may include a selectable marker. Suitable selectable markers may include one or more of the genes for ampicillin resistance, streptomycin resistance, kanamycin resistance, tetracycline resistance, chloramphenicol resistance, and sulfonamide resistance, operationally linked to a suitable promoter (e.g., a constitutive promoter). In one embodiment, the DNA plasmid includes the gene for kanamycin resistance.

The DNA plasmid may include sequences required for maintaining and/or replicating the plasmid in one or more suitable host cells. In one embodiment, the DNA plasmid is capable of functioning as a shuttle vector between suitable host cells. The DNA plasmid may be capable of functioning as a shuttle vector between *A. succinogenes* and *E. coli*.

Also disclosed is a host cell that includes one or more of the aforementioned DNA molecules. For example, the host cell may comprise a DNA plasmid that includes the DNA molecule. The host cell may be suitable for producing and isolating a DNA plasmid that includes the DNA molecule.

The host cell may be suitable for producing one or more organic acids in a fermentation system. In some embodiments, the host cell expresses a Zwf gene (and subsequently a Zwf enzyme) at a level suitable for enhancing the production or one or more organic acids (e.g., succinic acid or lactic acid) in a fermentation system. In some embodiments, the host cell may expresses a Zwf gene (and subsequently a Zwf enzyme) at a level suitable for enhancing the concentration of reducing equivalents (e.g., NADPH) in the host cell. The host cell may comprise a recombinant strain of *A. succinogenes* that expresses a Zwf gene (and subsequently a Zwf enzyme) at a level suitable for enhancing the concentration of reducing equivalents (e.g., NADPH) in the strain. Such a strain may be suitable for producing enhanced levels of succinic acid in a fermentation system relative to a strain that does not comprise the recombinant DNA molecule.

In some embodiments, the host cell is capable of producing succinic acid at concentrations of at least about 20 g/L, 40 g/L, 60 g/L, 80 g/L, 100 g/L, 120 g/L, 140 g/L, and/or 160 g/L (e.g., in a fermentation system). In certain embodiments, the host cell is capable of producing succinic acid at concentrations of at about 50 g/L to about 130 g/L. Desirably, the host cell does not produce selected organic acids other than succinic acid at substantial concentrations. Where the host cell produces organic acids other than succinic acid (e.g., acetic acid, formic acid, pyruvic acid, and mixtures thereof), desirably the organic acids other than succinic acid are produced at concentrations no more than about 30 g/L, more desirably no more than about 20 g/L, more desirably no more than about 10 g/L, and even more desirably no more than about 5 g/L.

The aforementioned recombinant microorganisms may be used in methods that include fermenting a nutrient medium to produce one or more organic acids. In some embodiments, the methods may include fermenting a nutrient medium with a recombinant microorganism that expresses a Zwf gene (e.g., the E. coli Zwf gene). Organic acids produced by the method may include succinic acid and lactic acid. In further embodiments, the methods are suitable for producing succinic acid at concentrations of at least about 20 g/L, 40 g/L, 60 g/L, 80 g/L, 100 g/L, 120 g/L, and/or 160 g/L.

In particular, the methods may include fermenting a nutrient medium with a recombinant strain of A. succinogenes that expresses a Zwf gene (and subsequently a Zwf enzyme) at a level suitable for enhancing the production of an organic acid (e.g., succinic acid). The Zwf gene may include a heterologous Zwf gene. A recombinant strain of A. succinogenes that expresses a heterologous Zwf gene (i.e., the E. coli Zwf gene) is deposited under ATCC accession number PTA-6255. In certain embodiments, the recombinant microorganism is a recombinant strain of a microorganism such as Bisgaard Taxon 6 or Bisgaard Taxon 10 that expresses a Zwf gene (which may be heterologous) at a level suitable for enhancing the production of an organic acid (e.g., succinic acid). Suitable recombinant microorganisms also include recombinant strains of E. coli that express a Zwf gene (which may be heterologous) at a level suitable for enhancing the production of an organic acid (e.g., lactic acid).

In the method, it may be desirable to ferment a nutrient medium with recombinant microorganisms that produce relatively high levels of selected organic acids, such as succinic acid and/or lactic acid. As such, the selected recombinant microorganisms may be resistant to high levels of organic acids, such as succinic and/or lactic acid. The recombinant microorganisms may also be selected to produce relatively low levels of other undesirable by-products. For example, the recombinant microorganism may produce relatively low levels of acetate, formate, pyruvate, and mixtures thereof (e.g., no more than about 2.0 g/L, no more than about 2.0 g/L formate, and/or no more than about 3.0 g/L pyruvate). The above-described recombinant microorganisms that are resistant to concentrations of sodium monofluoroacetate of about 1 g/L, 2 g/L, 4 g/L, and/or 8 g/L are suitable for the method.

In the method, the nutrient medium typically includes a fermentable carbon source. A fermentable carbon source may be provided by a fermentable biomass. In one embodiment, the fermentable carbon source is derived from feedstock, including sugar crops, starch crops, and/or cellulosic crop residues. Generally, the fermentable carbon source is a sugar, such as glucose. The fermentable carbon source may also include sugar alcohols. In suitable embodiments, the method results in a succinic acid yield (g) of at least about 100% relative to glucose (g).

BRIEF DESCRIPTION OF THE DRAWINGS

FIG. 1: Metabolic flux analysis of A. succinogenes variant FZ45 batch fermentation using glucose.

FIG. 2: Metabolic flux analysis of recombinant A. succinogenes FZ45/pJR762.73 batch fermentation using glucose.

FIG. 3: Zwf enzymatic activities in cell extracts of transformed strains. Extracts were prepared and assayed for Zwf activity as described below. All strains carrying pJR762.73 showed orders of magnitude increases in Zwf activity, which is graphed on a logarithmic scale.

DETAILED DESCRIPTION OF THE PREFERRED EMBODIMENTS

Disclosed herein is a recombinant microorganism which expresses a polypeptide that has one or more biochemical activities of an enzyme utilized in the pentose phosphate cycle. As used herein, "microorganism" includes any suitable single-cell organism such as bacteria, fungi, and yeast. As used herein, "recombinant microorganism" means a microorganism that has been modified in a manner that results in a non-naturally occurring microorganism. A "recombinant microorganism" may include a microorganism that has been transformed with a DNA molecule (e.g., a recombinant DNA molecule).

A recombinant microorganism may include a microorganism that has been transformed with a DNA molecule that expresses a polypeptide having one or more biochemical activities of the Zwf enzyme. The pentose phosphate cycle utilizes several enzymes including glucose-6-phosphate-1-dehydrogenase, (also called Zwischenferment enzyme or Zwf); 6-phosphogluconolactonase; 6-phosphogluconate dehydrogenase, (also called Gnd); ribose-5-phosphate isomerase A and B; ribulose phosphate 3-epimerase; transketolase I and II; and transaldolase A and B. Of these enzymes, Zwf and Gnd result in the production of two hydrogen equivalents in the form of NADPH.

The recombinant microorganism may express any suitable polypeptide or variant thereof having one or more biochemical activities of the Zwf enzyme (e.g., glucose-6-phosphate-1-dehydrogenase activity and NADP reductase activity). For example, one suitable Zwf enzyme is the E. coli Zwf enzyme or a variant thereof. In some embodiments, the recombinant microorganism may express the Zwf enzyme at elevated levels (i.e., "overexpress" the enzyme) relative to levels present in non-recombinant microorganisms.

The recombinant microorganism may express a variant polypeptide having at least about 90% sequence identity to the amino acid sequence of a Zwf enzyme, and more desirably at least about 95% sequence identity to the amino acid sequence of a Zwf enzyme. In suitable embodiments, the recombinant microorganism may express a variant of a Zwf enzyme that has at least about 96%, 97%, 98%, or 99% sequence identity to the Zwf enzyme. Desirably, the variant polypeptide has one or more biochemical activities of the Zwf enzyme. A variant polypeptide may include a fragment of the Zwf enzyme. Suitable Zwf enzymes include A. succinogenes Zwf enzyme, E. coli Zwf enzyme, and variants thereof.

The recombinant microorganism may express a polynucleotide encoding a polypeptide having one or more biochemical activities of the Zwf enzyme such as a Zwf gene or a variant thereof. For example, the recombinant microorganism may express a Zwf gene or a variant comprising a DNA sequence that has at least about 90% sequence identity to the Zwf gene, and more desirably at least about 95% sequence identity to the Zwf gene. In suitable embodiments, the recombinant microorganism may express a variant of the Zwf gene comprising a DNA sequence that has at least about 96%, 97%, 98%, or 99% sequence identity to the Zwf gene. Desirably, the variant polynucleotide encodes a polypeptide having one or more biochemical activities of Zwf enzyme. A variant polynucleotide may include a fragment of the Zwf gene. In some embodiments, the recombinant microorganism may express an *A. succinogenes* Zwf gene, an *E. coli* Zwf gene, or a variant thereof.

The recombinant microorganism may be derived from any suitable microorganism. Typically, the microorganism is capable of producing an organic acid at a level suitable for commercial production. As used herein, an "organic acid" includes at least one carboxylic group. For example, "organic acid" includes succinic acid and lactic acid. As used herein, organic acids may be alternately designated by the organic acid anion or a salt thereof. For example, "succinic acid" may be referred to as "succinate"; "lactic acid" may be referred to as "lactate"; "formic acid" may be referred to as "formate"; and "pyruvic acid" may be referred to as "pyruvate."

Suitable microorganisms for preparing recombinant microorganisms as described herein may include, but are not limited to, members of the *Actinobacillus* genus, including *A. succinogenes*; Bisgaard Taxon 6; Bisgaard Taxon 10; Mannheimia succiniciproducens; *E. coli*; *Anaerobiospirillum succiniciproducens*; *Ruminobacter amylophilus*; *Succinivibrio dextrinosolvens*; *Prevotella ruminicola*; *Ralstonia eutropha*; and coryneform bacteria (e.g., *Coryizebacterium glutamicum*, *Corynebacterium ammoniagenes*, *Brevibacterium flavum*, *Brevibacterium lactofermentuin*, *Brevibacterium divaricatum*); members of the *Lactobacillus* genus; yeast (e.g., members of the *Saccharomyces* genus); and any subset thereof. Suitable microorganisms for preparing recombinant microorganisms as described herein may include succinic acid producing microorganisms.

The recombinant microorganism typically expresses a Zwf gene, which may be a heterologous Zwf gene. The Zwf gene may be optimized for expression in the recombinant microorganism. For example, the Zwf gene may be operationally linked to a promoter that facilitates overexpression of the gene in the recombinant microorganism relative to a non-recombinant microorganism. The promoter may be endogenous to the microorganism (i.e., native to the microorganism from which the recombinant microorganism is derived) or heterologous to the microorganism (i.e., not native to the microorganism from which the recombinant microorganism is derived or obtained from a source other than the microorganism). The promoter may be endogenous to the Zwf gene or heterologous to the Zwf gene (i.e., a non-Zwf gene promoter). The promoter may facilitate constitutive and/or inducible expression of the Zwf gene, and/or the promoter may be modified to facilitate constitutive and/or inducible expression of the Zwf gene by suitable methods.

The Zwf gene may be modified to facilitate translation of the corresponding mRNA. For example, the Zwf gene may be modified to include codons that are not present in the endogenous or native gene. These non-endogenous codons may be selected to reflect the codon usage frequency in the recombinant microorganism. Codon usage tables have been developed for many microorganisms and are known in the art. The Zwf gene may be modified to reflect the codon usage frequency for *A. succinogenes* as provided below:

Exemplary Codon Frequency Usage for *Actinobacillus succinogenes*.

Source: GenBank Release 144.0 [Nov. 12, 2004]

| Triplet [frequency per thousand] | | | |
|---|---|---|---|
| UUU [20.4] | UCU [1.9] | UAU [13.0] | UGU [7.4] |
| UUC [29.7] | UCC [14.8] | UAC [16.7] | UGC [3.7] |
| UUA [35.3] | UCA [13.0] | UAA [1.9] | UGA [0.0] |
| UUG [20.4] | UCG [5.6] | UAG [0.0] | UGG [16.7] |
| CUU [13.0] | CCU [5.6] | CAU [5.6] | CGU [20.4] |
| CUC [1.9] | CCC [0.0] | CAC [7.4] | CGC [9.3] |
| CUA [0.0] | CCA [3.7] | CAA [18.6] | CGA [1.9] |
| CUG [5.6] | CCG [35.3] | CAG [3.7] | CGG [0.0]) |
| AUU [27.8] | ACU [18.6] | AAU [13.0] | AGU [7.4] |
| AUC [22.3] | ACC [31.5] | AAC [39.0] | AGC [3.7] |
| AUA [0.0] | ACA [5.6] | AAA [76.1] | AGA [1.9] |
| AUG [20.4] | ACG [18.6] | AAG [1.9] | AGG [0.0] |
| GUU [26.0] | GCU [13.0] | GAU [33.4] | GGU [61.2] |
| GUC [7.4] | GCC [13.0] | GAC [29.7] | GGC [24.1] |
| GUA [11.1] | GCA [22.3] | GAA [64.9] | GGA [0.0] |
| GUG [27.8] | GCG [35.3] | GAG [5.6] | GGG [5.6] |

The recombinant microorganism may include a recombinant strain of *A. succinogenes* that expresses a Zwf gene (e.g., an endogenous Zwf gene and/or a heterologous Zwf gene such as the *E. coli* Zwf gene). Other suitable microorganisms for producing recombinant microorganisms include Bisgaard Taxon 6 (deposited with the Culture Collection, University of Goteborg, Sweden (CCUG), under accession number 15568); Bisgaard Taxon 10 (deposited under CCUG accession number 15572); and any suitable strain of *E. coli* for which many strains are known in the art. The recombinant microorganism may be derived from a strain that produces high levels of one or more organic acids such as succinic acid and lactic acid, and/or the recombinant microorganism may be selected and/or engineered to produce high or enhanced levels of one or more organic acids such as succinic acid and lactic acid relative to a non-recombinant microorganism.

The recombinant microorganism may be derived from strains that are resistant to relatively high levels of undesirable by-products and/or strains of microorganisms that produce relatively low levels of undesirable by-products. Undesirable by-products may include formate (or formic acid), acetate (or acetic acid), and/or pyruvate (or pyruvic acid). Methods for selecting strains that produce low levels of acetate are known in the art. See, e.g., U.S. Pat. Nos. 5,521,075 and 5,573,931, which are incorporated herein by reference. For example, strains of microorganisms that produce relatively low levels of acetate may be selected by growing the microorganisms in the presence of a toxic acetate derivative, such as sodium monofluoroacetate at a concentration of about 1.0 to about 8.0 g/L. Selected strains may produce relatively low levels of acetate (e.g., less than about 2.0 g/L), formate (e.g., less than about 2.0 g/L), and/or pyruvate (e.g., less than about 3.0 g/L) in a glucose fermentation. One suitable monofluoroacetate resistant strain for producing a recombinant microorganism is a strain of *A. succinogenes* called FZ45, which is a derivative of *A. succinogenes* deposited under ATCC accession number 55618. See U.S. Pat. No. 5,573,931, which describes suitable methods for preparing microbial strains that are resistant to monofluoroacetate.

The recombinant microorganism may be selected and/or engineered to be resistant to relatively high levels of undesirable by-products and/or to produce relatively low levels of undesirable by-products. For example, after transformation, a population of recombinant microorganisms may be grown in the presence of sodium monofluoroacetate to select strains that are resistant to relatively high levels of acetate and/or strains that produce relatively low levels of acetate.

A DNA sequence that encodes a polypeptide with one or more biochemical activities of the Zwf enzyme may be obtained by employing methods known in the art (e.g., PCR amplification of a Zwf gene with suitable primers and cloning into a suitable DNA vector). The polynucleotide sequences of suitable Zwf genes have been disclosed. (See, e.g., GenBank). For example, the polynucleotide sequence of the *A. succinogenes* Zwf gene has been published (SEQ ID NO:5 & 6). (See Joint Genome Institute, Department of Energy website). The *E. coli* Zwf gene is deposited with GenBank (e.g., under GenBank Accession Number NC_000913 (SEQ ID NO:1) and GenBank Accession Number M55005 (SEQ ID NO:2)). The Zwf gene or variants thereof may be obtained by PCR amplification of a microorganism's genomic DNA with appropriate primers.

The DNA vector may be any suitable vector for expressing the gene in a recombinant microorganism. Suitable vectors include plasmids, artificial chromosomes (e.g., bacterial artificial chromosomes), and/or modified bacteriophages (e.g., phagemids). The vector may be designed to exist as an epigenetic element and/or the vector may be designed to recombine with the genome of the microorganism.

The DNA molecule typically includes a promoter operationally linked to a polynucleotide that encodes a polypeptide having Zwf enzyme activity. The promoter may be endogenous or native to the microorganism from which the recombinant microorganism is derived, or heterologous to the microorganism (i.e., derived from a source other than the recombinant microorganism). Furthermore, the promoter may be the native promoter for a selected Zwf gene or may be a promoter other than the native promoter for a selected Zwf gene (i.e., a non-Zwf gene promoter). Where the recombinant microorganism is a strain of *A. succinogenes*, a suitable endogenous or native promoter is the *A. succinogenes* phosphoenolpyruvate (PEP) carboxykinase promoter (SEQ ID NO:4), deposited under GenBank accession number AY308832, including nucleotides 1-258, or a variant thereof. The promoter may be operationally linked to the Zwf gene using cloning methods that are known in the art. For example, the promoter and Zwf gene may be amplified by PCR using primers that include compatible restriction enzyme recognition sites. The amplified promoter and gene then may be digested with the enzyme and cloned into an appropriate vector that includes a suitable multiple cloning site.

In addition, the DNA molecule may include a selectable marker. The selectable marker may impart resistance to one or more antibiotic agents. For example, selectable markers may include genes for ampicillin resistance, streptomycin resistance, kanamycin resistance, tetracycline resistance, chloramphenicol resistance, sulfonamide resistance, or combinations of these markers. Typically, the selectable marker is operationally linked to a promoter that facilitates expression of the marker. Plasmids and other cloning vectors that include selectable markers are known in the art.

The DNA molecule typically is used to transform a host cell. Suitable host cells include any cell that is useful for storing and/or producing the DNA molecule.

Suitable host cells may include cells that expresses any gene present on the DNA molecule. Suitable host cells also may include cells that are capable of producing an organic acid in a fermentation process, such as succinic acid at a concentration suitable for commercial production (e.g., at least about 20 g/L, more suitably at least about 50 g/L, and more suitably at least about 100 g/L).

The methods for producing an organic acid typically include fermenting a nutrient medium with a recombinant microorganism that expresses a Zwf gene. For example, the method may include fermenting a nutrient medium with a recombinant *A. succinogenes* that expresses a Zwf gene (e.g., a heterologous Zwf gene such as the *E. coli* Zwf gene). Organic acids produced in the fermentation may include succinic acid. One suitable recombinant microorganism for the methods is a recombinant strain of *A. succinogenes* that expresses the *E. coli* Zwf gene, deposited under ATCC accession number PTA-6255. The methods also may include fermenting a nutrient medium with a recombinant strain of Bisgaard Taxon 6 or Bisgaard Taxon 10 that express a Zwf gene (e.g., a heterologous Zwf gene such as the *E. coli* Zwf gene) to produce succinic acid. The methods also may include fermenting a nutrient medium with a recombinant strain of *E. coli* that expresses a Zwf gene (or overexpresses a Zwf gene) to produce one or more organic acids such as lactic acid.

The methods may employ recombinant microorganisms that are resistant to relatively high levels of the organic acid being produced (e.g., succinic acid). The methods also may employ strains of microorganisms that are resistant to relatively high levels of undesirable by-products and/or strains of microorganisms that produce relatively low levels of undesirable by-products.

The nutrient medium typically includes a fermentable carbon source. The fermentable carbon source may be provided by a fermentable biomass. A fermentable biomass may be derived from a variety of crops and/or feedstocks including: sugar crops (e.g., sugar, beets, sweet sorghum, sugarcane, fodder beet); starch crops (e.g., grains such as corn, wheat, sorghum, barley, and tubers such as potatoes and sweet potatoes); cellulosic crops (e.g., corn stover, corn fiber, wheat straw, and forages such as Sudan grass forage, and sorghum). The biomass may be treated to facilitate release of fermentable carbon source (e.g., sugars). For example, the biomass may be treated with enzymes such as cellulase and/or xylanase, to release simple sugars. The fermentable carbon source may include simple sugars and sugar alcohols such as glucose, maltose, mannose, mannitol, sorbitol, galactose, xylose, arabinose, and mixtures thereof.

The methods typically result in a relatively high yield of succinic acid relative to an input carbon source such as glucose. For example, the methods may have a succinic acid yield (g) of at least about 90% relative to glucose input (g). Alternatively, the yield may be calculated as % succinic acid yield (mol)/glucose input (mol). As such, the methods may have a succinic acid yield (mol) of at least about 140% relative to glucose input (mol). Desirably, the methods may have a succinic acid yield (mol) of at least about 130% or at least about 170% relative to glucose input (mol).

The methods also typically result in a relatively high concentration of succinic acid production (e.g., relative to a method that uses a non-recombinant microorganism in a fermentation). For example, a fermentation may reach a concentration of at least about 50 g/L succinic acid. Desirably, a fermentation may reach a concentration of at least about 90 g/L succinic acid or more desirably, a concentration of at least about 130 g/L succinic acid. In some embodiments, the fermentation typically does not produce substantial levels of undesirable by-products such as acetate, formate, pyruvate, and mixtures thereof (e.g., no more than about 2.0 g/L acetate, no more than about 2.0 g/L formate, and/or no more than about 3.0 g/L pyruvate).

The methods may be used to produce relatively high concentration of lactic acid (e.g., relative to a method that uses a non-recombinant microorganism in a fermentation). For example, the recombinant microorganisms may be used in a fermentation to produce lactic acid at a concentration of at least about 25 g/L. In one embodiment, the fermentation yields may yield about 0.5 g lactic acid per gram glucose. The methods for producing lactic acid may include fermenting a suitable carbon source with recombinant *E. coli* that expresses (or overexpresses) a polypeptide that has one or more biochemical activities of the Zwf gene. For example, the method may include fermenting a suitable carbon source with recombinant *E. coli* that expresses the *E. coli* Zwf gene from an epigenetic element such as a plasmid.

Illustrated Embodiments

In one embodiment, the recombinant microorganism is a recombinant strain of *Actinobacillus succinogenes* that expresses a heterologous Zwf gene. The heterologous Zwf gene may be optimized for expression in *Actinobacillus succinogenes*. The heterologous Zwf gene may encode an *E. coli* Zwf enzyme. The recombinant strain may include recombinant *Actinobacillus succinogenes* deposited under ATCC Accession Number PTA-6255. The recombinant strain may be capable of producing succinic acid at concentrations of about 50 g/L to about 130 g/L (e.g., in a fermentation system that utilizes a suitable carbon source). The recombinant strain may be resistant to levels of sodium monofluoroacetate of at least about 1 g/L.

In some embodiments, the recombinant strain is a recombinant strain of microorganism belonging to Bisgaard Taxon 6 or Bisgaard Taxon 10 that expresses a heterologous Zwf gene. The heterologous Zwf gene may encode *E. coli* Zwf enzyme.

In another embodiment, the recombinant strain is a recombinant strain of *Actinobacillus succinogenes*, which includes a DNA molecule comprising a transcription promoter for *Actinobacillus succinogenes* operationally linked to a heterologous Zwf gene. The transcription promoter may include the *A. succinogenes* phosphoenolpyruvate (PEP) carboxykinase promoter or a variant thereof (e.g., a polynucleotide of SEQ ID NO:4 or a polynucleotide having at least about 95% sequence identity to SEQ ID NO:4, where the polynucleotide has *A. succinogenes* phosphoenolpyruvate (PEP) carboxykinase promoter activity). The heterologous Zwf gene may encode *E. coli* Zwischenferment enzyme or a variant thereof (e.g., a polynucleotide of SEQ ID NO:1 or a polynucleotide having at least about 95% sequence identity to SEQ ID NO:1, where the polynucleotide has *E. coli* Zwischenferment enzyme activity). The heterologous Zwf gene may include the *E. coli* Zwf gene. Optionally, the Zwf gene may be optimized for expression in *Actinobacillus succinogenes*. The DNA molecule may be epigenetic (e.g., present on a plasmid). The DNA molecule may include a selectable marker (e.g., kanamycin resistance, ampicillin resistance, streptomycin resistance, sulfonamide resistance, tetracycline resistance, chloramphenicol resistance, or a combination thereof).

In another embodiment, the recombinant strain is a recombinant strain of *Actinobacillus succinogenes* which comprises a heterologous Zwf enzyme. The heterologous Zwf enzyme may be expressed from a Zwf gene that has been optimized for expression in *Actinobacillus succinogenes*. The heterologous Zwf enzyme may include *E. coli* Zwischenferment enzyme. The recombinant strain may include recombinant *A. succinogenes* deposited under ATCC Accession Number PTA-6255. The recombinant strain may be capable of producing succinic acid at concentrations of about 50 g/L to about 130 g/L. Optionally, the recombinant strain is resistant to levels of sodium monofluoroacetate of at least about 1 g/L.

In one embodiment, the method for producing succinic acid includes fermenting a nutrient medium with a recombinant microorganism that expresses a heterologous Zwf gene. The recombinant microorganism may include a recombinant strain of *Actinobacillus succinogenes* (e.g., *A. succinogenes* recombinant strain deposited under ATCC Accession Number PTA-6255). The recombinant microorganism may include a recombinant strain of Bisgaard Taxon 6 or a recombinant strain of Bisgaard Taxon 10. The heterologous Zwf gene may include the *E. coli* Zwf gene. Optionally, the recombinant strain is resistant to levels of sodium monofluoroacetate of at least about 1 g/L. Optionally, the recombinant strain is capable of producing succinic acid at concentrations of about 50 g/L to about 130 g/L. The nutrient medium may include a fermentable sugar (e.g., glucose). Typically, the method results in a succinic acid yield (g) of at least about 100% relative to glucose (g).

In one embodiment, the recombinant DNA molecule includes a transcription promoter for *A. succinogenes* operationally linked to a heterologous Zwf gene. For example, the transcription promoter may include the *A. succinogenes* phosphoenolpyruvate (PEP) carboxykinase promoter or a variant thereof, (e.g., a polynucleotide of SEQ ID NO:4 or a polynucleotide having at least about 95% sequence identity to SEQ ID NO:4, where the polynucleotide has *Actinobacillus succinogenes* phosphoenolpyruvate (PEP) carboxykinase promoter activity).

In one embodiment, the recombinant DNA molecule is present in a DNA plasmid. Typically, the DNA plasmid includes a selectable marker (e.g., a gene selected from the group consisting of ampicillin resistance, kanamycin resistance, streptomycin resistance, tetracycline resistance, chloramphenicol resistance, sulfonamide resistance, and combinations thereof). The DNA molecule, which may be present in a DNA plasmid, may be present in a host cell. The host cell may be capable of producing succinic acid at concentrations of about 50 g/L to about 130 g/L in a fermentation system.

In one embodiment, the recombinant microorganism is a recombinant strain of a succinic acid producing microorganism which has been transformed with a DNA molecule that expresses a polypeptide having Zwf enzyme activity. The DNA molecule may include a polynucleotide that encodes a polypeptide having Zwf enzyme activity, which may include NADP reductase activity. The DNA molecule may include a polynucleotide that encodes a polypeptide having at least about 90% sequence identity (or desirably at least about 95% sequence identity) to the amino acid sequence of a Zwf enzyme (e.g., SEQ ID NO:3 or SEQ ID NO:6), where the polypeptide has Zwf enzyme activity (e.g., NADP reductase activity). The DNA molecule may include a polynucleotide sequence having at least about 90% sequence identity (or desirably at least about 95% sequence identity) to the polynucleotide sequence of a Zwf gene (e.g., SEQ ID NO:1; SEQ ID NO:2; or SEQ ID NO:5), where the polynucleotide encodes a polypeptide having Zwf enzyme activity. In some embodiments, the recombinant strain may be derived from a microorganism whose 16S rRNA has at least about 90% sequence identity to 16S rRNA of *Actinobacillus succinogenes*. For example, the recombinant strain may be derived from a strain of *Actinobacillus succinogenes*, Bisgaard Taxon 6, or Bisgaard Taxon 10.

In another embodiment, the recombinant microorganism is a recombinant strain of a succinic acid producing microorganism that has been transformed with a heterologous Zwf gene. The heterologous Zwf gene may be optimized for expression in the microorganism. In some embodiments, the heterologous Zwf gene may encode *E. coli* Zwf enzyme. In some embodiments, the Zwf gene may include a polynucleotide having at least about 95% sequence identity to SEQ ID NO:1, where the polynucleotide has Zwf enzyme activity.

In another embodiment, the recombinant microorganism is a recombinant strain of a succinic acid producing microorganism that has been transformed with a DNA molecule that includes a transcription promoter for phosphoenolpyruvate (PEP) carboxykinase operationally linked to polynucleotide encoding a polypeptide having Zwf enzyme activity. The transcription promoter may include the *Actinobacillus succinogenes* phosphoenolpyruvate (PEP) carboxykinase promoter. In some embodiments, the promoter may include a polynucleotide having at least about 95% sequence identity to SEQ ID NO:4, where the polynucleotide has promoter activity.

In another embodiment, the recombinant microorganism is a recombinant strain transformed with a DNA molecule that is epigenetic. The DNA molecule may be present on a plasmid.

In another embodiment, the recombinant microorganism is a recombinant strain that is capable of producing succinic acid at concentrations of about 50 g/L to about 130 g/L.

The recombinant strain may be resistant to levels of sodium monofluoroacetate of at least about 1 g/L. In some embodiments, the recombinant strain is recombinant *Actinobacillus succinogenes* deposited under ATCC Accession Number PTA-6255.

In another embodiment, the recombinant microorganism is used for producing succinic acid in a method that include fermenting a nutrient medium with the recombinant microorganism. The nutrient medium typically includes fermentable sugar such as glucose. The method may result in a succinic acid yield (g) of at least about 100% relative to glucose (g).

In some embodiments, the DNA molecule comprising a transcription promoter for a succinic acid producing microorganism operationally linked to a heterologous Zwf gene. The transcription promoter may include a phosphoenolpyruvate (PEP) carboxykinase promoter. In some embodiments, the promoter includes a polynucleotide having at least about 95% sequence identity to SEQ ID NO:4, where the polynucleotide has promoter activity. The DNA molecule may be present within a plasmid. The DNA molecule may be present in a host cell (e.g., a host cell capable of producing succinic acid at concentrations of about 50 g/L to about 130 g/L).

EXAMPLES

Microorganism Strains and Plasmids

*A. succinogenes* strain FZ45 is a stable bacterial variant of *Actinobacillus succinogenes* 130Z, which is resistant to sodium monofluoroacetate. See Guettler et al., INT'L J. SYST. BACT. (1999) 49:207-216; and U.S. Pat. No. 5,573,931. The *E. coli-A. succinogenes* shuttle vector pLS88 (deposited at the American Type Culture Collection as ATCC accession no. 86980) was obtained from Dr. Leslie Slaney, University of Manitoba, Canada. Plasmid pLS88 is described as having been isolated from *Haenzophilus ducreyi* and may confer resistance to sulfonamides, streptomycin, and kanamycin.

Genetic Manipulations

Recombinant DNA manipulations generally followed methods described in the art. Plasmid DNA was prepared by the alkaline lysis method. Typical resuspension volumes for multicopy plasmids extracted from 1.5 ml cultures were 50 µl. Larger DNA preparation used the Qiagen Plasmid Purification Midi and Maxi kit according to the manufacturer's instructions. Restriction endonucleases, Molecular Weight Standards, and pre-stained markers were purchased from New England Biolabs and Invitrogen and digests were performed as recommended by the manufacturers, except that an approximately 5-fold excess of enzyme was used. DNA was analyzed on Tris-acetate-agarose gels in the presence of ethidium bromide. DNA was extracted from agarose gels and purified using the Qiagen gel extraction kit according to the manufacturer's instructions. DNA was dephosphorylated using shrimp alkaline phosphatase (Roche) in combination with restriction digests. The phosphatase was heat inactivated at 70° C. for 15 min. Ligations were performed using a 3- to 5-fold molar excess of insert to vector DNA in a 20 µl reaction volume and 1 µl of T4 DNA Ligase (New England Biolabs) for 1 hour at 25° C. *E. coli* transformation were performed by using "library efficiency competent cells" purchased from Invitrogen, following the manufacturer's instructions.

Transformations using ligation mixes were plated without dilutions on standard LB plates containing the appropriate antibiotic. PCR amplifications were carried out using the Perkin Elmer manual as a guideline. Primer designs were based on published sequences (as provided at the National Center for Biotechnology Information (NCBI) database). The primers included engineered restriction enzyme recognition sites. Primers were analyzed for dimer and hairpin formation and melting temperature using the Vector NTI program. All primers were ordered from the Michigan State Macromolecular Structure Facility. PCR amplifications were carried out in an Eppendorf Gradient Master Cycler, or in a Perkin Elmer Thermocycler. Starting annealing temperatures were determined using the Vector NTI program for each primer pair. Restriction enzymes for digesting the amplified products were purchased from Invitrogen or New England Biolabs.

Plasmid pJR762.55

The *A. succinogenes* phosphoenolpyruvate (PEP) carboxykinase promoter sequence ($P^{pepck}$, SEQ ID NO:4, GenBank accession number AY308832, including nucleotides 1-258) was amplified from *A. succinogenes* FZ45 genomic DNA using the following primers: Forward, 5'-AAA GAATTCTTAATTTCTTTAATCGGGAC (SEQ ID NO:7); and Reverse, 5'-GCGTCGACATACTTCACCTCATTGAT (SEQ ID NO:8). EcoRI and SalI restriction sequences (underlined nucleotides) were included to facilitate cloning, and the resulting 0.27-kb $P^{pepck}$ fragment was inserted as an EcoRI/SalI fragment into pLS88 to produce plasmid pJR762.55.

Plasmid pJR762.73

The Zwf gene from *E. coli* was amplified from strain BL21 (DE3) genomic DNA (ATCC accession number NC_000913), using the following primers: Forward, 5'-CCGCTCGAGGGCGGTAACGCAAACAGC (SEQ ID NO:9); and Reverse, 5'-CCGCTCGAGTTACTCAAACT-CATTCCAGG (SEQ ID NO:10). XhoI restriction sequences (underlined nucleotides) were included to facilitate cloning and the ensuing 1.5 kb Zwf fragment was inserted into the SalI site of pJR762.55 to produce plasmid pJR762.73. Transformation of *A. succinogenes*

*A. succinogenes* competent cells for electroporation were prepared by growing cells in tryptic soy broth medium (TSB) to an $OD_{600}$ of ~0.6. Cells were spun down, washed twice with sterile water, twice with 10% v/v glycerol and resuspended in 0.01× the original culture volume with 10% glycerol. Cells were flash frozen and stored at minus 80° C. Approximately 40 µl of thawed cells were used for electroporation, in 0.1 cm cuvettes with a BioRad GenePulser at settings of 400 W, 25 mF, and 1.8 kV. Following electroporation, 1 ml room temperature TSB medium was immediately added and the cells were incubated at 37° C. for 1 h. The cell solution was plated on TSB agar plates containing Kanamycin (100 µg/ml).

Optical Density Determination of *A. succinogenes*

Samples from magnesium-neutralized fermentations were spun at 420×g for 2 min to precipitate the MgCO$_3$ and diluted with 0.5N HCl to solubilize any remaining precipitate before reading at OD$_{660}$.

*A. succinogenes* Batch Fermentations

*A. succinogenes* fermentations were performed in 5 l fermentors containing the following medium unless otherwise specified: 80 g/L glucose, 85 g/L liquid feed syrup (LFS), 0.2 mg/L biotin, 5 mM phosphate, 3 g/L yeast extract, Sensient AG900. The pH was maintained at 7.0 with a Mg(OH)$_2$. Agitation was set at 250 rpm, temperature at 38° C., and carbon dioxide was sparged at a rate of 0.025 v.v.m. Fermentors were inoculated with a 1.25% Seed inoculum, raised in serum vials containing the medium described above. The fermentation medium for recombinant strains of *A. succinogenes* contained 100 µg/ml Kanamycin.

Clearing of LFS

For fermentations that required a measure of growth through optical density measurements a cold water extract of LFS was used. Suspended solids and some oils were removed through centrifugation of LFS in a Sorvall GSA rotor, at 9,000 rpm for 20 minutes. The supernatant was allowed to settle in a separation funnel for 3 hours at room temperature. The lower water phase typically represented 57% (w/v) of the raw LFS.

Biochemical Assays to Verify Zwf Expression

Glucose-6-phosphate dehydrogenase assays were performed as described by Choi et al., 2003. (See Choi, Jae-Chulk, Shin, Hyun-Dong, Lee, Yong-Hyun (2003) *Enzyme and Microbial Technology* 32, p. 178-185; "Modulation of 3-*hydroxyvalerate molar fraction on poly*(3-*Ihydroxybutyrate*-3-*hydroxyvalerate*) *using Ralstonia eutropha transformant co-amplifying phbC and NADPH generation-related Zwf genes*"). The formation rate of D-6-phospho-glucono-δ-lactone was measured by the increase in NADPH, which was quantified by measuring the absorbance at 340 nm. Each assay was performed in 1 ml containing, 50 µl [1M] Tris-HCl, pH 7.5, 200 µl [50 mM] MgCl$_2$, 100 µl [10 mM] NADP, 100 µl [10 mM] glucose-6-phosphate, 450 µl H2O, and 100 µl cell extract. The specific activity was calculated as: Specific Activity=dA/dt/0.623×(protein concentration), or µmol/min mg$^{-1}$. Increased Zwf activity was observed in all recombinant strains that include the plasmid pJR762.73, which expresses the *E. coli* Zwf gene from the *A. succinogenes* PEPCK promoter. Increased activity was observed in transformed *Actinobacillus* strain (FZ45) and in transformed strains of Bisgaard Taxon 6 (BT6) and Bisgaard Taxon 10 (BT10), which carried the plasmid pJR762.73. These results are illustrated in FIG. 3.

*E. coli* Fermentations

*E. coli* strains DH5α/pJR762.73 (Zwf), DH5α/pJR762.17 (Zwf), and DH5α/pLS88 were grown in NBS 5-liter Bioflo III fermentors using four liters of the following medium: 900AG yeast extract 15 g; corn steep liquor 15 g; Na$_2$HPO$_4$ 1.16 g; NaH$_2$PO$_4$H$_2$O, 0.84 g: (NH$_4$)$_2$SO$_4$ 3 g; MgSO$_4$.7H$_2$O, 0.61; CaCl$_2$.2H$_2$O, 0.25 g, and glucose, 45 g per liter. The pH was controlled at 6.7 through the automatic addition of K$_2$CO$_3$ (3.3N). The fermentations were each started with a 1.25% inoculum. Conditions were initially made aerobic which favored the rapid growth of the *E. coli* cells; stirring was at 500 rpm and the medium was sparged with air at 0.5 liter/liter-min. Fermentor conditions were made anaerobic to favor organic acid production when the cell density reached a minimum of 6.2 OD$_{660}$ units; then the medium was sparged with 0.2 liter/liter-min of a CO$_2$ and H$_2$ mixture (95:5), and stirring was reduced to 250 rpm. Samples were taken periodically and the organic acid products and residual glucose concentrations were determined through HPLC.

Analysis of Fermentation Broths

Succinic acid, glucose, lactic acid, pyruvate, ethanol, and formic acid concentrations were determined by reverse phase high pressure liquid chromatography (HPLC) using a Waters 1515 Isocratic pump with a Waters 717 Auto sampler and a Waters 2414 refractive index detector set at 35° C. The HPLC system was controlled, data collected and processed using Waters Breeze software (version 3.3). A Bio-Rad Aminex HPX-87H (300 mm×7.8 mm) column was used with a cation H guard column held at 55° C. The mobile phase was 0.021 N sulfuric acid running at 0.5 ml/min. Samples were filter through a 0.45 µm filter, and 5.0 µl was injected onto the column. Run time was thirty minutes.

CO$_2$ Measurements

A mass flow controller (Brooks model 58501) was used to monitor and supply CO$_2$ to the fermentor sparging system at 100 ml/min. A mass flow meter (Brooks model 58601) was used to measure CO$_2$ exiting the fermentor by way of the exhaust condenser system. The two CO$_2$ flow meters were connected to a computer via a 4-20 ma Bio-Command Interface. The BioCommand Plus Bioprocessing software logged the inlet and outlet CO$_2$ flow every 60 seconds. The rate of CO$_2$ consumption (ml/min) was expressed as the difference between the inlet and outlet rates during any given minute (CO$_2$use=CO$_2$ in−CO$_2$out). The volume of CO$_2$ consumed during any given fermentation interval is the sum of rates each minute of the interval. The moles of CO$_2$ consumed were calculated using the Ideal Gas Law, (consumed liters/22.4 liters/mole=consumed moles).

The mass flow meters were calibrated by the manufacturer for CO$_2$ and their precision was 1% of full scale or 2 ml/m. The fermentation set-up was monitored for gas leaks by mixing 5% hydrogen into the CO$_2$. Hydrogen leaks were detected using a Tif8800 CO/Combustible Gas analyzer.

Metabolic Flux Analysis of *A. succinogenes* Fermentations

The metabolic flux distributions (MFA) during anaerobic succinic acid production in *Actinobacillus succinogenes* were analyzed using the FluxAnalyzer software package. The FluxAnalyzer package was obtained from Professor Steffen Klamt (Max Planck Institute, Magdeburg, Germany) and was operated according to the instructions provided in the manual. The FluxAnalyzer package facilitates the analysis of metabolic fluxes by providing a graphical user interface for the MATLAB program, which performs the actual mathematical calculations. The MATLAB software was purchased from MathWork Inc. By measuring the changes in extracellular concentrations of the known and expected components of the entire metabolic pathway, the intracellular fluxes for the major intracellular metabolites were calculated using the metabolic network model described below. The specific network (labeled A_succinogenes) was constructed using the 20 known metabolites and 27 reactions shown below (without considerations of biomass composition and growth rate):

A_Succinogenes Metabolic Network Model

| A_succinogenes Metabolic Network Model | |
|---|---|
| Glucose (in) → Glucose | (R1) |
| Glucose → Glucose-6P | (R2) |
| Glucose-6P + 2 NAD → 2 PEP + 2 NADH | (R3) |

-continued

| A_succinogenes Metabolic Network Model | |
|---|---|
| PEP → Pyruvate | (R4) |
| PEP + $CO_2$ → OAA | (R5) |
| Pyruvate → Pyruvate (out) | (R6) |
| Pyruvate + NAD → Acetyl-coA + NADH + $CO_2$ | (R7) |
| Pyruvate + NADH + $CO_2$ → Malic acid | (R8) |
| Acetyl-coA → Acetate | (R9) |
| Acetate → Acetate (out) | (R10) |
| Acetate + OAA → Citrate | (R11) |
| Citrate + NAD → $CO_2$ + NADH + α-KG | (R12) |
| OAA + NADH → Malic acid + NAD | (R13) |
| Malic acid → Fumarate | (R14) |
| Fumarate + NADH → Succinic acid + NAD | (R15) |
| Succinic acid → Succinic acid (out) | (R16) |
| $CO_2$ (in) → $CO_2$ | (R17) |
| Glycerol (in) → Glycerol | (R18) |
| Glycerol + 2 NAD → PEP + 2 NADH | (R19) |
| Sorbitol (in) → Sorbitol | (R20) |
| Sorbitol + NAD → Glucose-6P + NADH | (R21) |
| Xylose (in) → Xylose | (R22) |
| Xylose → R5P | (R23) |
| R5P + 5/3 NAD → 5/3 PEP + 5/3 NADH | (R24) |
| Glucose-6P + 2 NADP → R5P + $CO_2$ + 2 NADPH | (R25) |
| Acetyl-coA + 2 NADH → Ethanol + 2 NAD | (R26) |
| Ethanol → Ethanol (out) | (R27) |

Fermentation samples were analyzed over the time course of the fermentations using the analytical methods previously described. Concentrations of glucose, glycerol, arabinose, xylose, sorbitol, succinic acid, acetic acid, ethanol, pyruvate, lactic acid and fermentation volumes were determined at each sampling time. The amount of metabolite was calculated according to the formula: (metabolite, g)=V (fermentor, 1)*C (metabolite, g/l). The metabolite consumption rate or the metabolite production rate during the time period of $t_0$–$t_1$ was calculated using the formula: Metabolite consumption rate (mol/h, $t_0$ and $t_1$)=[Amount (metabolite, g, $t_0$)–Amount (metabolite, g, $t_1$)]/[($t_1$–$t_0$)*Molecular Weight of Metabolite]. For comparison of metabolic flux for all the time periods, the consumption rate or production rate of metabolite in the flux map was adjusted, assuming a glucose consumption rate in the flux map of 100. The metabolite consumption or production rate in the map "Mcp" was determined according to the following formula: Mcp=(metabolic consumption/or production rate)×100/(glucose consumption rate).

The consumption or production rates of the various metabolites were input into the metabolic network model in the FluxAnalyzer package according to the operating instructions. The function "Calculate/Balance Rates" was used to calculate all the calculatable rates. If the system was non-redundant, an optimization procedure was started, where a linear objective function was minimized. If the system was redundant, one or more of three methods (simple least squares, variances-weighted least squares I and variances weighted least squares II) were applied to calculate the rates. The flux rate was shown directly on the flux map. Final flux map were copied into Microsoft Excel files for storage purposes.

Metabolic Flux Analysis of Biochemical Pathways in *A. succinogenes* FZ45

Metabolic flux analysis was used to evaluate the effect of different carbon sources on succinic acid production in batch fermentations with *A. succinogenes* FZ45. The analyses established that the major pathway for succinic acid production in *A. succinogenes* FZ45 flows in the following manner: phosphoenolpyruvate (PEP→*oxaloacetate (OAA)→malate→fumarate→succinic acid. The glyoxylate shunt and the PEP-transport-system (PTS) appear not to be substantially used in the organism. Glucose fermentations reach a concentration of 61.7 g/L succinic acid with a yield of about 94% (succinic acid (g)/glucose (g)). Fermentations performed using a more reduced carbon source, such as sorbitol, produced higher amounts of succinic acid (77.3 g/L) with a higher yield (108% succinic acid (g)/glucose (g)), indicating that reducing power may become a limiting factor during the fermentation of glucose.

Enhanced Succinic Acid Production from Glucose by Over-Expression of Zwf

Strains FZ45, FZ45/pLS88 and FZ45/pJR762.73 were cultured under standard production conditions with the exception that 100 μg/ml Kanamycin was added to the fermentation medium for the transformed strains. FZ45/pLS88 served as a second control, and is transformed with the cloning vector, carrying no PEP carboxykinase promoter or Zwf gene. The carbon source used was glucose. The strain FZ45/pJR762.73 showed an increase in succinic acid production over the control strains FZ45 and FZ45/pLS88, with a corresponding increase in the final concentration of succinic acid. The total amount of succinic acid produced from glucose increased from 284 g to 302 g, the molar yield of succinic acid produced increased from 144% to 155% (moles succinic acid/100 moles glucose), the weight yield increased from 94.7% to 101.9%, and the final concentration of succinic acid in the fermentation broth increased from 62 g/L to 65 g/L. These results are summarized in Table 1. All transformed FZ45 derivatives exhibit slower growth compared to the untransformed FZ45, which may be caused by the replication of the additional extrachromosomal plasmid DNA.

TABLE 1

Production of Succinic acid From Glucose by Strains FZ45, FZ45/pLS88 and FZ45/pJR762.73

| Strain | Molar yield (%) | Weight yield (%) | g/L | Total Succinic acid [g] |
|---|---|---|---|---|
| FZ45 | 144 | 94.7 | 61.7 | 284 |
| FZ45/pLS88 | 149 | 98.0 | 60.4 | 272 |
| FZ45/pJR762.73 | 155 | 101.9 | 65.4 | 302 |

Further, the strain FZ45/pJR762.73 also produced less of the two metabolites acetic acid and pyruvic acid, as shown in Table 2.

TABLE 2

Production of Other Metabolites by Strains FZ45 and FZ45/pJR762.73

| Strain | Succinic Acid [g/l] | Pyruvic Acid [g/l] | Acetic Acid [g/l] |
|---|---|---|---|
| FZ45 | 61.7 | 3.7 | 1.5 |
| FZ45/pLS88 | 60.4 | 2.1 | 1.4 |
| FZ45/pJR762.73 | 65.4 | 2.7 | 1.4 |

Metabolic flux analyses on both FZ45 and FZ45/pJR762.73 showed that FZ45/pJR762.73 channeled more carbon into the pentose phosphate pathway than the untransformed FZ45 (See FIG. 1 and FIG. 2). Thus, over-expression of the Zwf protein was sufficient to enhance succinic acid yields and to reduce the production of other metabolites when glucose was used as carbon source.

Fermentation with *A. succinogenes* FZ45/pJR762.73 Using a Reduced Carbon Source Fermentations with *A. succinogenes* FZ45/pJR762.73 utilizing mannitol as a carbon source were also performed.

Mannitol is a 6-carbon sugar-alcohol that is more reduced than glucose. Expression of Zwf also enhanced succinic acid production using mannitol (See Table 3). However, fermentations using this sugar alcohol also showed increased yields even with the untransformed strain FZ45. This indicates that increasing the amount of metabolic reducing equivalents will enhance succinic acid production.

TABLE 3

Production of Succinic Acid Using Mannitol as Carbon Source

| Strain | Carbon Source | Molar yield (%) | Weight yield (%) | g/L | Succinic Acid [total g] |
|---|---|---|---|---|---|
| FZ45 | glucose | 144 | 94.7 | 61.7 | 284 |
| FZ45 | mannitol | 179 | 116.0 | 85 | 406 |
| FZ45/pJR762.73 | mannitol | 193 | 125.4 | 88 | 421 |

Effect of Zwf Expression in Recombinant Bisgaard Taxon 6 and Bisgaard Taxon 10

The effect of Zwf expression in other species was also tested using the organisms Bisgaard Taxon 6 (BT6) and Bisgaard Taxon 10 (BT10). Both organisms belong to the family *Pasteurellaceae*, and are related to *A. succinogenes*. Also, both organisms are known to produce succinic acid. Using the methods described above and the same plasmid, pJR762.73 (carrying the Zwf gene under the *A. succinogenes* PEPCK promoter), Bisgaard Taxa were transformed. Both these transformed strains showed an increase in succinic acid production using glucose as the carbon source. These results are shown in Table 4 below.

TABLE 4

Production of Succinic acid from Glucose by Strains BT6/pJR762.73 and BT10/pJR762.73

| Strain | Molar yield (%) | Weight yield (%) | g/L | Succinic Acid [total g] |
|---|---|---|---|---|
| BT6/pLS88 | 92 | 60.3 | 40 | 174 |
| BT6/pJR762.73 | 96 | 62.8 | 39 | 180 |
| BT10/pLS888 | 132 | 86.5 | 56 | 255 |
| BT10/pJR762.73 | 136 | 89.0 | 57 | 258 |

Flux analysis of these fermentations with the Bisgaard Taxa strains indicated that use of the pentose phosphate pathway was indeed increased in the strains carrying the plasmid. BT6/pJR762.73 routed more carbon through the pentose phosphate pathway than the control (33 mol % vs. 20 mol %). Similarly, BT10/pJR762.73 routed 35 mol % carbon through the pentose phosphate pathway, compared to only 5 mol % in the control.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

All references, patents, and/or applications cited in the specification are incorporated by reference in their entireties, including any tables and figures, to the same extent as if each reference had been incorporated by reference in its entirety individually.

The invention claimed is:

1. A genetically-modified microorganism of the family *Pasteurellaceae* that is transformed with at least one polynucleotide sequence encoding a glucose-6-phosphate dehydrogenase enzyme that is operably linked to a promoter sequence, wherein said microorganism produces an increased amount of succinic acid compared to a parent microorganism that is not transformed with the at least one polynucleotide sequence.

2. A genetically-modified microorganism according to claim 1, wherein said microorganism comprises a 16S ribosomal RNA sequence with at least 90% sequence identity to the 16S ribosomal RNA sequence of *Actinobacillus succinogenes*.

3. A genetically-modified microorganism according to claim 2, wherein said polynucleotide encodes an *Esherichia coli* glucose-6-phosphate dehydrogenase enzyme.

4. A genetically-modified microorganism according to claim 2, wherein said promoter sequence comprises a phosphoenolpyruvate carboxykinase promoter operably linked to said polynucleotide encoding the glucose-6-phosphate dehydrogenase enzyme.

5. A genetically-modified microorganism according to claim 4, wherein the microorganism is capable of producing succinic acid at concentrations of about 50 g/L to 130 g/L.

6. A genetically-modified microorganism according to claim 2, wherein said polynucleotide encodes at least one *Actinobacillus succinogenes* glucose-6-phosphate dehydrogenase enzyme.

7. A genetically-modified microorganism according to claim 6, which comprises a phosphoenolpyruvate carboxykinase promoter operably linked to said polynucleotide encoding an *Actinobacillus succinogenes* glucose-6-phosphate dehydrogenase enzyme.

8. A genetically-modified microorganism according to claim 7, wherein said promoter is an *Actinobacillus succinogenes* promoter.

9. A genetically-modified microorganism according to claim 8, wherein the microorganism is capable of producing succinic acid at concentrations of about 50 g/L to 130 g/L.

10. A genetically-modified microorganism according to claim 1, wherein the microorganism is capable of producing succinic acid at concentrations of about 50 g/L to 130 g/L.

11. A genetically-modified microorganism according to claim 2, wherein the polynucleotide is a variant having at least 90 percent sequence identity to a glucose-6-phosphate dehydrogenase gene.

12. A genetically-modified microorganism according to claim 11, wherein the polynucleotide variant enzyme has at least 95 percent sequence identity to a glucose-6-phosphate dehydrogenase gene.

13. A method of producing succinic acid, comprising culturing a genetically-modified microorganism according to claim 1 under conditions sufficient to produce succinic acid.

14. A method of producing succinic acid comprising culturing a genetically-modified microorganism according to claim 2, under conditions sufficient to produce succinic acid.

15. A genetically-modified microorganism according to claim 1, wherein said promoter sequence is operably linked to a polynucleotide encoding an endogenous glucose-6-phosphate dehydrogenase enzyme and wherein said promoter sequence and said polynucleotide are integrated into the genome of the microorganism.

16. A method of producing succinic acid comprising culturing a genetically-modified microorganism according to claim 4 under conditions sufficient to produce succinic acid at concentrations of about 50 g/L to 130 g/L.

* * * * *